US010022119B2

(12) United States Patent
Widmer

(10) Patent No.: US 10,022,119 B2
(45) Date of Patent: Jul. 17, 2018

(54) DEVICES AND METHODS FOR SECURING TISSUE TO BONE

(71) Applicant: Benjamin Widmer, Salt Lake City, UT (US)

(72) Inventor: Benjamin Widmer, Salt Lake City, UT (US)

(73) Assignee: Benjamin Widmer, Salt Lake City, UT (US)

( * ) Notice: Subject to any disclaimer, the term of this patent is extended or adjusted under 35 U.S.C. 154(b) by 128 days.

(21) Appl. No.: 15/152,834

(22) Filed: May 12, 2016

(65) Prior Publication Data

US 2016/0331366 A1 Nov. 17, 2016

Related U.S. Application Data

(60) Provisional application No. 62/160,777, filed on May 13, 2015, provisional application No. 62/161,392, filed on May 14, 2015, provisional application No. 62/253,397, filed on Nov. 10, 2015.

(51) Int. Cl.
 A61B 17/04 (2006.01)
 A61B 17/06 (2006.01)
 A61B 90/92 (2016.01)
 A61B 90/94 (2016.01)

(52) U.S. Cl.
 CPC .... *A61B 17/0401* (2013.01); *A61B 17/06166* (2013.01); *A61B 90/92* (2016.02); *A61B 90/94* (2016.02); *A61B 2017/044* (2013.01); *A61B 2017/0414* (2013.01)

(58) Field of Classification Search
 CPC .......... A61B 17/0401; A61B 17/06166; A61B 90/92; A61B 90/94; A61B 2017/044; A61B 2017/0414
 See application file for complete search history.

(56) References Cited

U.S. PATENT DOCUMENTS

| 5,534,011 | A | * | 7/1996 | Greene, Jr. | ........ | A61B 17/0485 606/232 |
| 5,709,708 | A | * | 1/1998 | Thal | .................... | A61B 17/0401 606/232 |
| 5,964,783 | A | * | 10/1999 | Grafton | .............. | A61B 17/0401 606/232 |
| 7,226,469 | B2 | * | 6/2007 | Benavitz | ............ | A61B 17/0401 606/232 |
| 8,840,643 | B2 | * | 9/2014 | Dreyfuss | ............ | A61B 17/0401 606/232 |
| 2002/0052629 | A1 | * | 5/2002 | Morgan | ............. | A61B 17/0401 606/232 |

(Continued)

*Primary Examiner* — Son Dang
(74) *Attorney, Agent, or Firm* — Workman Nydegger

(57) ABSTRACT

An orthopedic ligation assembly includes a bone anchor having an eyelet and a suture line formed in a continuous loop and loaded onto the bone anchor, the suture line passing through the eyelet of the bone anchor to form a first looped portion on a first side of the bone anchor and a second looped portion on a second side of the bone anchor. The suture line can be pre-loaded onto the bone anchor prior to implantation of the bone anchor in a configuration that prevents unloading of the suture line from the anchor. The suture line can include a plurality of differentiable sections providing a surgeon with the ability to differentiate separate portions of the suture line during an orthopedic procedure.

18 Claims, 24 Drawing Sheets

(56) References Cited

U.S. PATENT DOCUMENTS

| | | | |
|---|---|---|---|
| 2003/0060835 A1* | 3/2003 | Wenstrom, Jr. | A61B 17/0401 606/148 |
| 2004/0106950 A1* | 6/2004 | Grafton | A61B 17/0401 606/232 |
| 2007/0073299 A1* | 3/2007 | Dreyfuss | A61B 17/0401 606/326 |
| 2007/0150003 A1* | 6/2007 | Dreyfuss | A61B 17/0401 606/232 |
| 2007/0219558 A1* | 9/2007 | Deutsch | A61B 17/0401 606/326 |
| 2007/0225764 A1* | 9/2007 | Benavitz | A61B 17/0401 606/232 |
| 2009/0287246 A1* | 11/2009 | Cauldwell | A61B 17/0401 606/232 |
| 2009/0318962 A1* | 12/2009 | Spedden | A61B 17/06166 606/228 |
| 2011/0313453 A1* | 12/2011 | Krumme | A61B 17/0401 606/232 |
| 2011/0319932 A1* | 12/2011 | Avelar | A61B 17/0469 606/228 |
| 2012/0158051 A1* | 6/2012 | Foerster | A61B 17/0401 606/232 |
| 2014/0371767 A1* | 12/2014 | Ostapoff | A61L 17/105 606/151 |
| 2016/0331366 A1* | 11/2016 | Widmer | A61B 17/0401 |

* cited by examiner

DEVICES AND METHODS FOR SECURING TISSUE TO BONE

CROSS-REFERENCE TO RELATED APPLICATIONS

This application claims the benefit of U.S. Provisional Patent Application No. 62/160,777, filed May 13, 2015, U.S. Provisional Patent Application No. 62/161,392, filed May 14, 2015, and U.S. Provisional Patent Application No. 62/253,397, filed Nov. 10, 2015, the disclosures of which are incorporated herein in their entirety.

BACKGROUND

Orthopedic procedures often require the attachment of soft tissue to bone and/or the attachment of one section of bone to another section of bone. Typically, such procedures are carried out by implanting one or more bone anchors into a bone surface and using one or more suture lines which have been passed through an eyelet of the bone anchor to join the target tissue or bone to the bone surface. However, typical bone anchor and suture line assemblies require a configuration that can make it difficult for a surgeon to manage, track, and organize the separate suture line portions extending from the surgical site.

In addition, typical suture line configurations can increase the risk that a surgeon may accidentally unload the suture line from the anchor by incorrectly manipulating the suture line, e.g., by confusing separate portions of the suture line, and/or by pulling a portion of the suture line too far. Such unloading can render the unloaded anchor useless and/or can complicate the surgery and increase overall surgery time and cost. Furthermore, the portion of the suture line engaged with the eyelet of the anchor can often represent a weak spot in the tissue repair, limiting the overall strength of the repair and increasing the risk of suture failure.

For at least these reasons, there is an ongoing need to provide alternative and/or additional orthopedic ligation devices, assemblies, and methods. Such devices, assemblies, and methods should be capable of providing suture line configurations that allow a surgeon to manage, track, and organize the separate suture line portions extending from the surgical site. In addition, such devices, assemblies, and methods should reduce the risk of accidental unloading of the suture line from the bone anchor and should provide sufficient strength to the tissue-to-bone or bone-to-bone repair. At least some of the embodiments disclosed below are directed toward these objectives.

BRIEF SUMMARY

The present disclosure describes systems, methods, and assemblies for securing a target tissue to a bone surface or for securing separate bone segments or surfaces together. The embodiments described herein can be used in any tissue-to-bone or bone-to-bone application.

In certain embodiments, an orthopedic ligation assembly includes a bone anchor having an eyelet and a suture line formed in a continuous loop and loaded onto the bone anchor, with the suture line passing through the eyelet of the bone anchor to form a first looped portion on a first side of the bone anchor and a second looped portion on a second side of the bone anchor.

In certain embodiments, the suture line can be loaded or pre-loaded onto the bone anchor (e.g., prior to implantation of the bone anchor) in a configuration that prevents unloading of the suture line from the anchor.

In certain embodiments, the suture line may include a plurality of differentiable sections allowing a surgeon to differentiate sections of the suture line during an orthopedic ligation procedure. The suture line may include visually and/or tactily differentiate sections.

In certain embodiments, an orthopedic ligation assembly may include a bone anchor having an eyelet and a suture line passing through the eyelet of the bone anchor to form a looped portion on a first side of the bone anchor and a first and second tail on a second side of the bone anchor, the first and second tails being formed by cutting a continuous loop. In such embodiments, the suture line can also include a knot, the first and second tails passing through the looped portion to form the knot.

In certain embodiments, the looped portion can be positioned at an outer side of a target tissue being secured by the assembly, the outer side being opposite the bone anchor, and wherein the first and second tails are passed around a portion of the target tissue and through the looped portion on the outer side to form the knot, and wherein the looped portion is positioned at the outer side of the target tissue by passing through the target tissue.

In certain embodiments, all portions of the suture line can be disposed between the body of the bone anchor and the target tissue pass through the eyelet of the bone anchor. In certain embodiments, the bone anchor has at least a double-loaded configuration with at least two strands of the suture line passing through the eyelet of the bone anchor.

Certain embodiments include a method of securing a target tissue to bone using an orthopedic assembly as disclosed herein, the method comprising: securing a bone anchor to bone, the bone anchor having a suture line loaded thereon, the suture line being formed in a continuous loop and passing through an eyelet of the bone anchor to form a first looped portion on a first side of the bone anchor and a second looped portion on a second side of the bone anchor; positioning the first looped portion at an outer side of the target tissue (e.g., by passing through the target tissue or by passing around a first side of the target tissue), the outer side being opposite the bone anchor; cutting the second looped portion of the suture line to form a first tail and a second tail; and passing the first and second tails around a portion of the target tissue (e.g., around a second side of the target tissue opposite the first side) and through the looped portion on the outer side of the target tissue to form a securing knot. In certain embodiments, a method further comprises cutting the first looped portion to form two separate strands of the suture line loaded onto the bone anchor.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. Embodiments of the disclosure will be described and explained with additional specificity and detail through the use of the accompanying drawings in which.

DETAILED DESCRIPTION

The present disclosure describes systems, methods, and assemblies for securing a target tissue to a bone surface or for securing separate bone segments or surfaces together. The embodiments described herein can be used in any tissue-to-bone or bone-to-bone application, such as applications involving the securing or fixation of a tendon or ligament, such as a bicep's tendon, glenoid labrum, rotator cuff tendon, pectoralis tendon or other tendon or ligament such as in a shoulder, knee, foot, ankle, hand, wrist, elbow, hip, or coraco-clavicular ligament reconstruction procedure, or in a bone fracture fixation procedure. Further, embodiments described herein are useful in percutaneous procedures. Various embodiments described herein relate to tissue-to-bone applications; however, one of skill in the art will recognize that the embodiments herein may be useful in a bone-to-bone application as well.

As used herein, the terms "suture line," "suture strand," and the like refer to any threadlike or filamentous material compatible with an orthopedic surgery application and capable of use in an orthopedic ligation procedure for securing tissue to bone or bone to bone. Suture lines can be monofilament or braided, and can be formed of any suitable material, preferably formed from a biocompatible polymer or combination of biocompatible polymers such as polyethylene, polyester, polybutylate, silicone, lactide, glycolide, etc. Suture lines can have a circular cross-section or a cross-section of any other shape, such as a suture "tape" having a rectangular cross-section.

As used herein, the term "anchor" refers to any device capable of being fixed within bone or to bone surface, and includes threaded anchors (e.g., screw in anchors), threadless anchors (e.g., push-in and/or friction fit anchors), and bone buttons, for example.

I. Tissue Ligation Assemblies

Figure 1A:
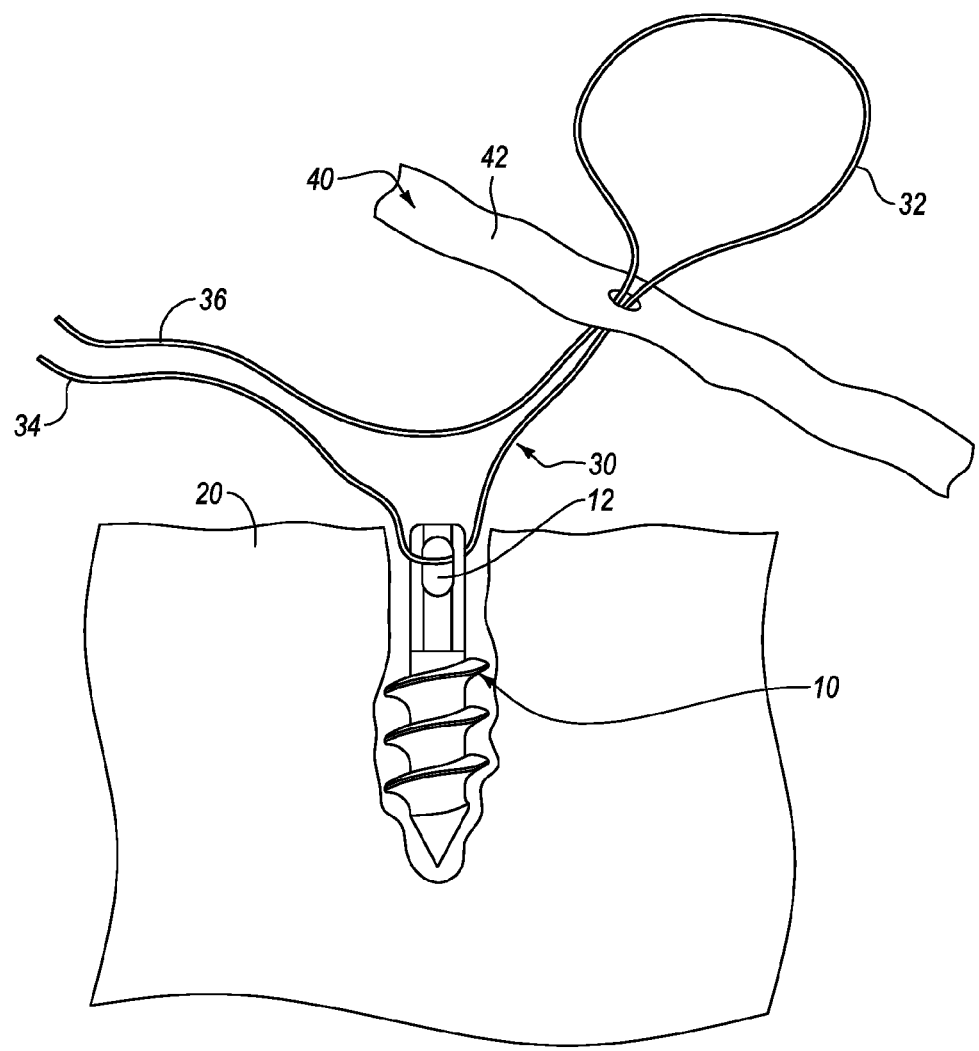
FIGS. 1A-1C illustrate a typical assembly and method for joining target tissue to bone.
Figure 1B:
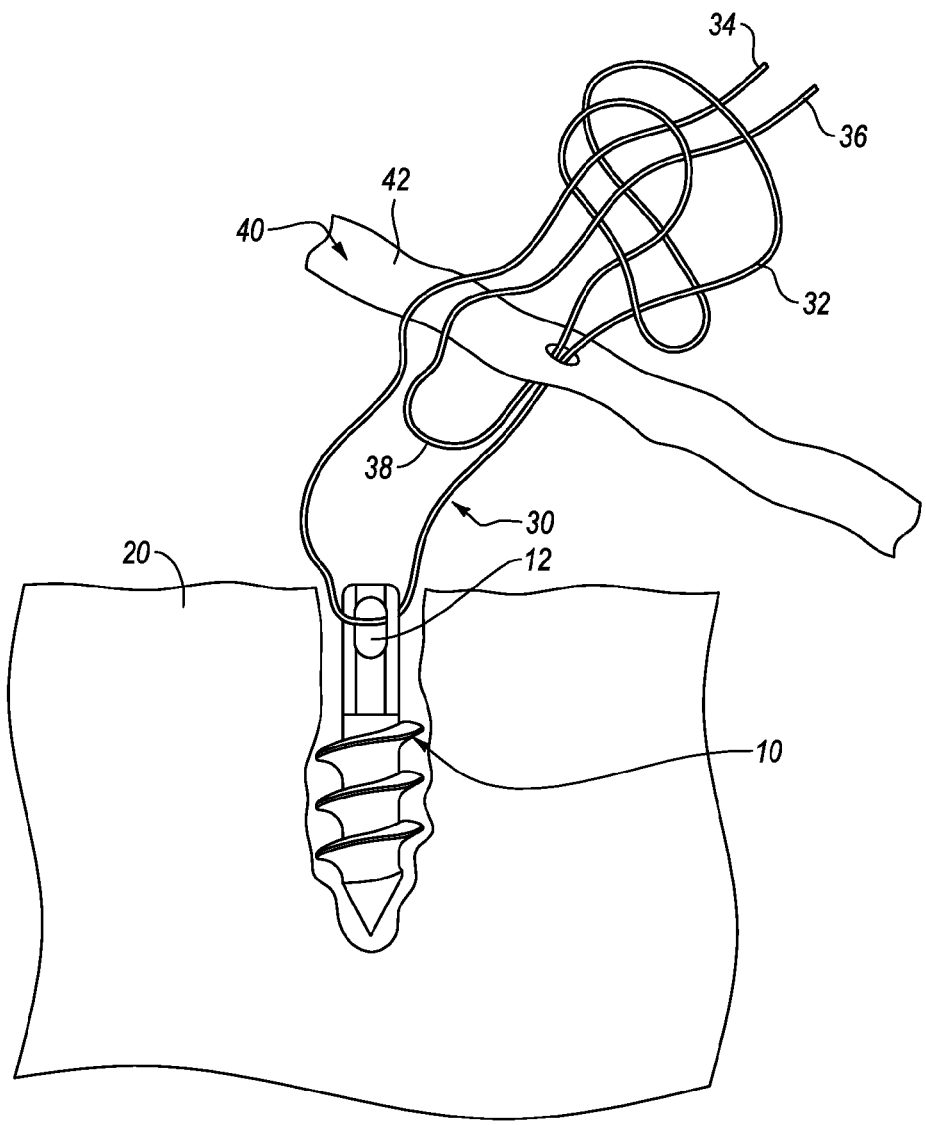
Figure 1C:
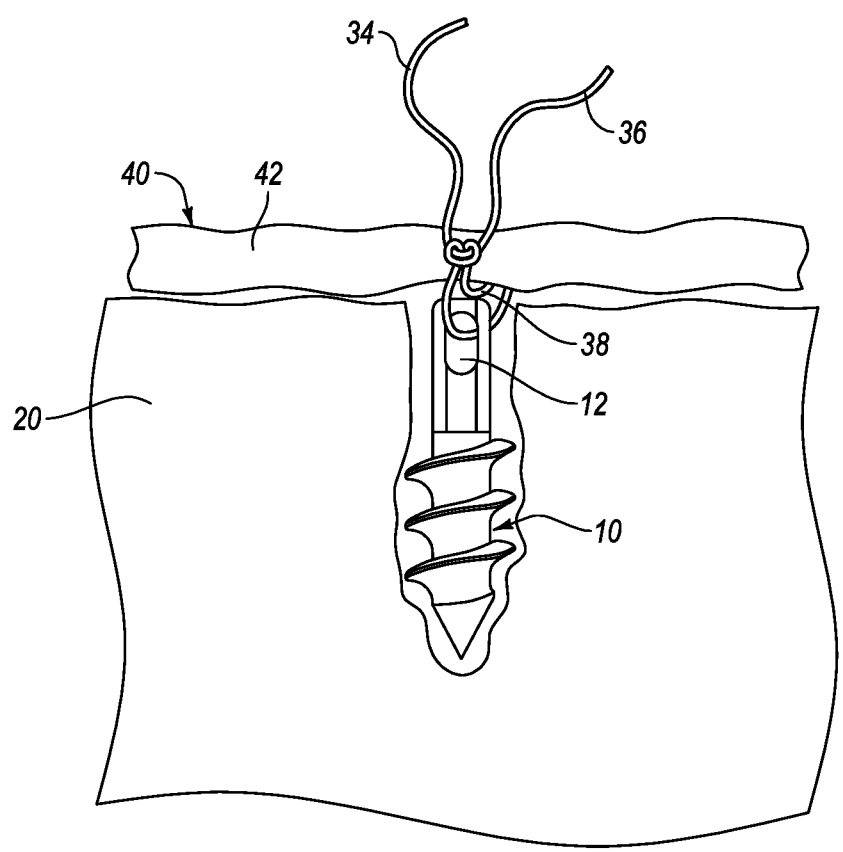

FIGS. 1A-1C illustrate a typical assembly and method for attaching a target tissue to bone. As shown in FIG. 1A, an anchor 10 is placed into bone surface 20 and a suture line 30 is passed through an eyelet 12 of the anchor 10. The suture line 30 is then passed through the target tissue 40. The resulting configuration consists of a looped portion 32 extending from a first side of the anchor 10 and an outer side 42 of the target tissue 40 and two free ends or tails 34 and 36 extending from a second side of the anchor 10 opposite the target tissue 40. A first tail 34 remains disposed through the eyelet 12 of the anchor 10 while a second tail 36 is free of any engagement with the anchor 10. From this configuration, a surgeon or operator may form a Rogozinski knot or other knot by forming a lark's head (i.e., a pair of adjacent loops) in the loop portion 32 of the suture line 30 and then passing the two tails 34 and 36 through the lark's head, as shown in FIG. 1B, to form the knot and bring the tissue into position against the bone anchor (shown tightened in FIG. 1C).

There are several limitations to this method. For example, it can be difficult to manage, track, and organize the two separate tail portions 34 and 36 and the looped portion 32, which, from the perspective of the surgeon, can look like four similar suture lines all extending from the surgical site. This is especially prone to occur in arthroscopic or endoscopic settings where visibility is limited. This can also increase the risk that a surgeon accidentally unloads the suture line 30 from the anchor 10 by wrongly manipulating the suture line 30, by confusing the separate tails 34 and 36, and/or by pulling a portion of the suture line 30 too far in any one direction. Such unloading can render the unloaded anchor useless and/or can complicate the surgery and increase overall surgery time and cost.

In addition, even successfully tied sutures resulting from this configuration will only be single loaded through the eyelet 12 of the bone anchor 10 (i.e., only one strand of the suture line is passed through the eyelet) as shown by tail 34. In some circumstances, the single portion of the suture line 30 engaged with the eyelet 12 of the anchor can represent a weak spot in the repair, limiting the overall strength of the repair and increasing the risk of suture failure.

Further, the final knot configuration leaves an unnecessary portion of suture material disposed between the tissue 40 and the bone surface 20. For example, as shown, the tail portion that is not passed through the eyelet 12 (tail 36 in the illustrated example) will, after being passed through the loop portion 32 to form the knot, leave a portion (shown as portion 38) undesirably disposed between the tissue 40 and the anchor 10. Likewise, in surgical procedures where the anchor 10 is fully disposed below the planar surface of the bone 20, as in FIGS. 1A-1C, the suture line portion that is not passed through the eyelet 12 will be partially and undesirably disposed between the tissue 40 and the surface of the bone 20, thereby possibly interfering with the tissue-to-bone interface despite not being passed through the anchor 10 to promote the strength of the repair at the anchor 10.

Figure 2A:
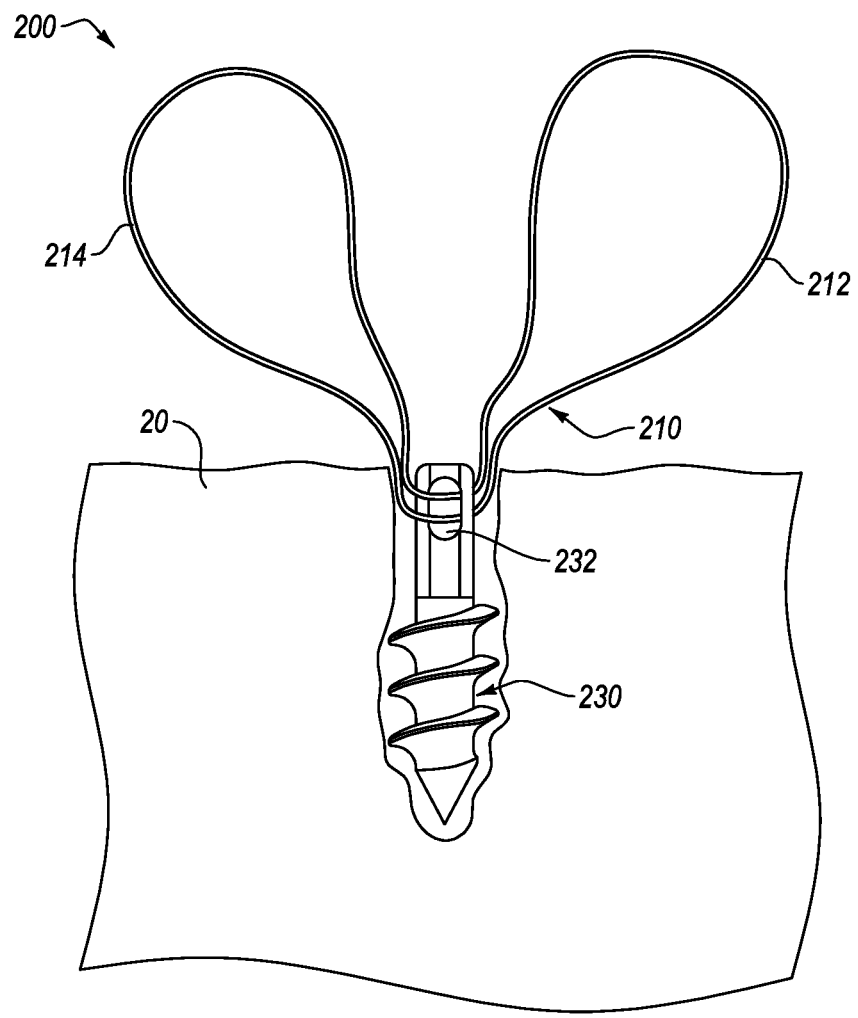
FIGS. 2A-2E illustrate an assembly and method according to the present disclosure for joining target tissue to bone.
Figure 2B:
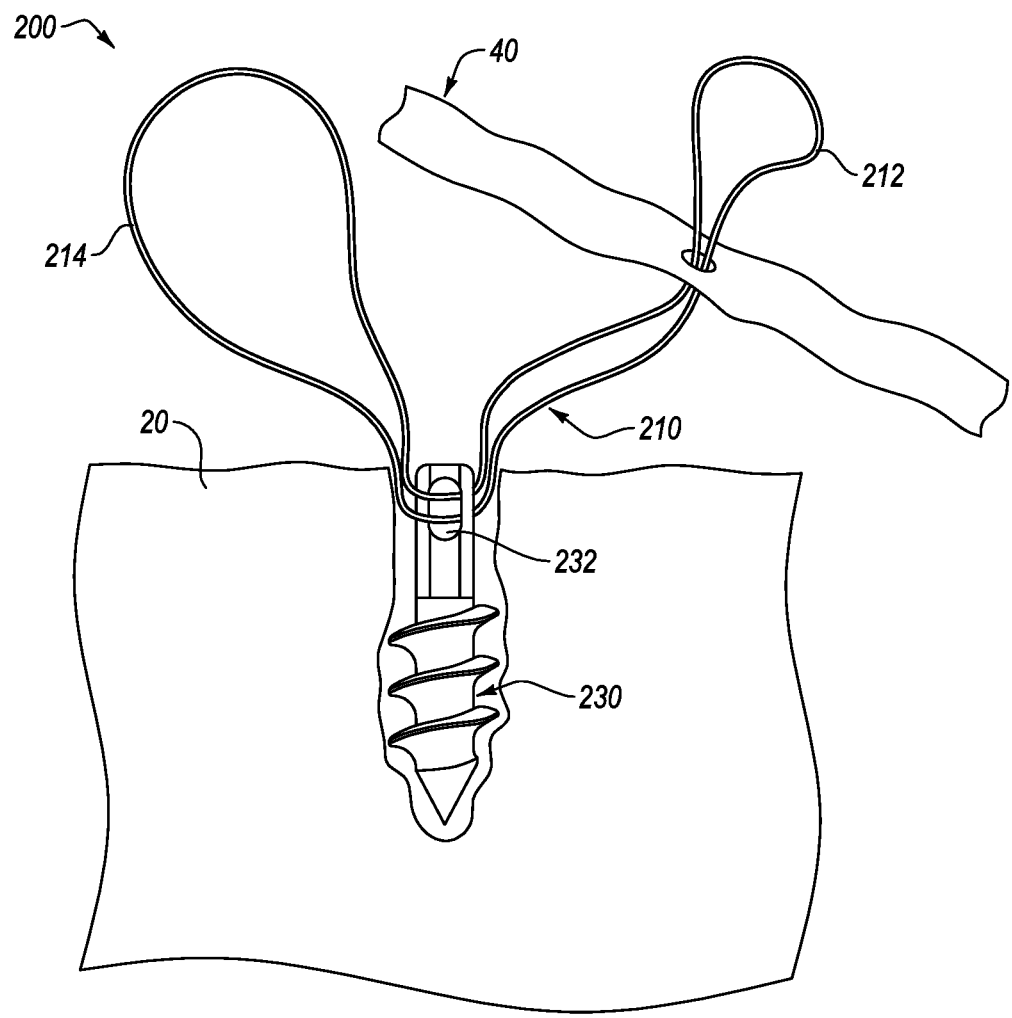

FIGS. 2A-2E illustrate an embodiment of an improved orthopedic ligation assembly 200. As illustrated, the assembly 200 can include a suture line configured in a continuous loop structure 210, the continuous loop 210 being passed through a passage (e.g., an eyelet 232) of an anchor 230 to form a first looped portion 212 and a second looped portion 214 on opposite sides of the anchor 230. In the illustrated embodiment, the continuous loop 210 is passed through a single eyelet 232 so as to leave two strands of the continuous loop 210 passing through the same eyelet 232. In this configuration, the suture line forms a first looped portion 212 on one side of the eyelet 232, converges at the eyelet 232, passes through the eyelet 232 as two strands, and extends out of the opposite side of the eyelet 232 to form the second looped portion 214 on the opposite side of the eyelet 232. As illustrated in FIG. 2B, the first looped portion 212 can be passed through the target tissue 40 that is to be secured to the anchor 230 and/or bone 20.

As illustrated in FIGS. 2A and 2B, the orthopedic ligation assembly advantageously provides a surgeon with the ability to easily control and manipulate the suture line by grasping each looped portion 212 and 214 (e.g., one in each hand) and moving each looped portion relative to the other in order to bring the suture line to a desired position and/or orientation. In addition, the first and second looped portions 212 and 214 are more easily managed and tracked, and the positional relationship between the handled portions is more readily apparent, than the suture line configuration illustrated in FIGS. 1A and 1B. For example, pulling on the first looped portion 212 of the embodiment of FIGS. 2A and 2B to lengthen the distance between the first looped portion 212 and the anchor 230 will result in a corresponding shortening of the distance between the second looped portion 214 and the anchor 230 and vice versa.

In another example, the suture line can be rotatably adjusted such that sections forming the first and second looped portions 212 and 214 are reversed with respect to the eyelet 232 (e.g., a section forming the first looped portion 212 can be passed through the eyelet 232 to a second side while a section forming the second looped portion 214 is correspondingly passed through the eyelet to a first side).

Figure 2C:
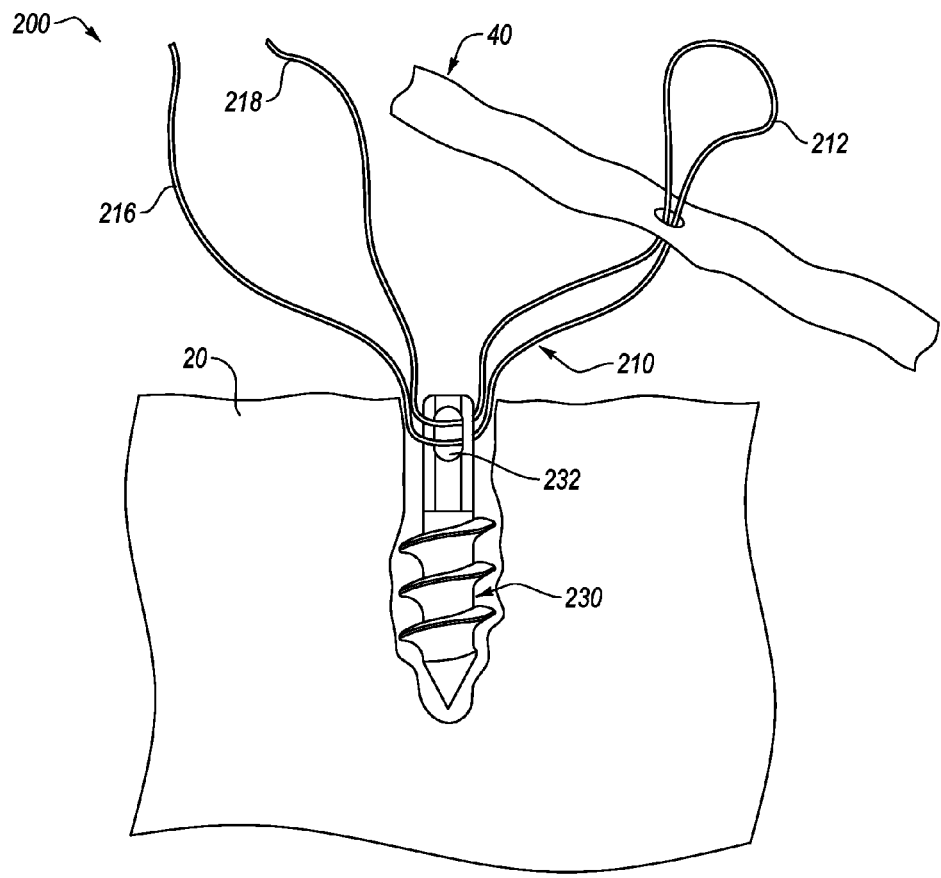
Figure 2D:
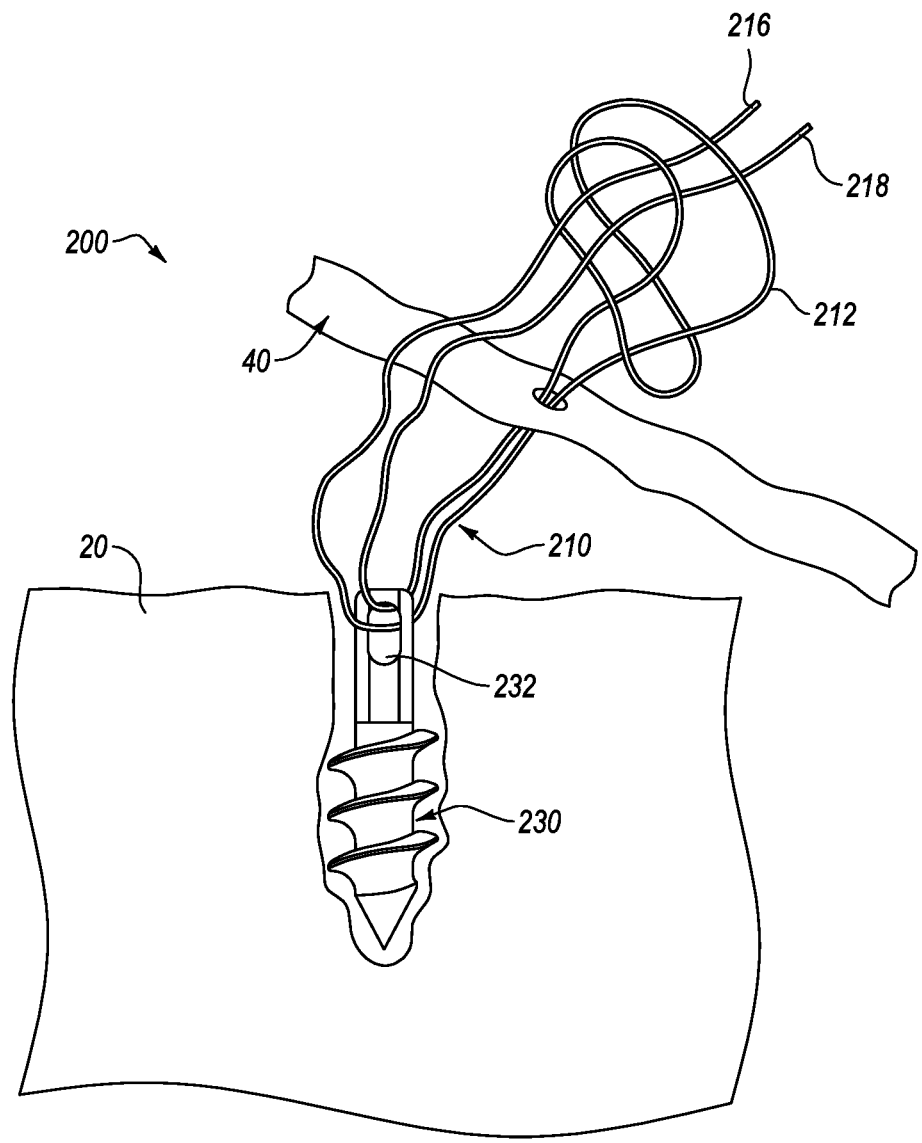
Figure 2E:
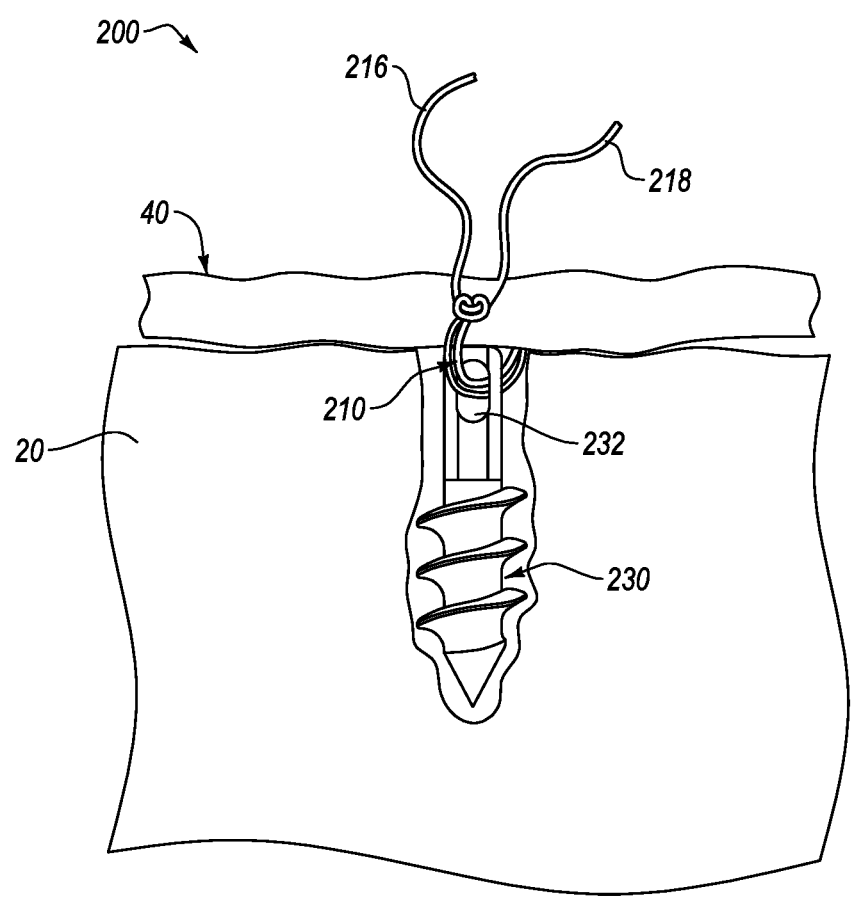

As illustrated in FIG. 2C, once the suture line is organized and oriented in the desired position, a surgeon may cut one of the looped portions to form two tails. In the illustrated embodiment, the second looped portion 214 (e.g., the looped portion not passing through the tissue) is cut to form two tails 216 and 218, though in other embodiments, the first looped portion 212 may be cut. The resulting configuration allows a surgeon to tie a knot by, for example, forming a lark's head (e.g., a pair of adjacent loops) in the looped portion 212 and passing the two tails 216 and 218 through the lark's head to form the suture knot, as illustrated in FIG. 2D (untightened) and FIG. 2E (tightened). It is within the meaning of the disclosure to utilize a Rogozinski knot, if so desired (as shown in FIGS. 2D and 2E). Rogozinski knots are described in U.S. Pat. No. 5,573,286, which is incorporated herein by this reference. Alternatively, other knots may be used to tie the suture line.

The embodiment illustrated in FIGS. 2A-2E provides several advantages and benefits. For example, having two looped portions provides ease of handling and positioning of the suture line relative to the anchor 230. In addition, after a knot is formed, two strands of the suture line are positioned as passed through the anchor and through the tissue, resulting in a double-loaded configuration having enhanced strength and durability relative to a single-loaded anchor with only a single thread passing through the anchor (such as in the knot shown in FIGS. 1B and 1C). Further, the positional relationship between the separate suture line portions provides easier management and tracking of the suture line. Even after a looped portion 214 has been cut, for example, the resulting two tails 216 and 218 will be similar in that each passes through the anchor 230, and they therefore will not necessarily need to be distinguished based on which single one passes through the anchor, as in the suture line configuration of FIGS. 1A-1C.

In addition, the orthopedic ligation assembly illustrated in FIGS. 2A-2E is able to provide a tissue-to-anchor and/or tissue-to-bone interface with minimal interference from the suture line. For example, the illustrated assembly 200 can bring the tissue 40 into contact with the anchor 230 and/or bone 20 without extraneous suture line material (e.g., suture line material not passing through the anchor 40) disposed between tissue 40 and the anchor 230 other than the suture line material actually passing through the anchor 230, thereby allowing a closer and/or tighter interface between the tissue 40 and the surface of the bone 20 to which it is secured.

Further, the orthopedic ligation assembly 200 illustrated in FIGS. 2A-2E can advantageously be placed and used for percutaneous anchor placement, such as a rotator cuff repair procedure, labral repair procedure, biceps tenodesis procedure, or other orthopedic procedure capable of being performed with (or necessitating) percutaneous anchor placement.

In some embodiments, the one or more suture lines forming continuous loops are each advantageously formed with a substantially uniform cross-section. For example, in some embodiments, a suture line forming a continuous loop has a diameter that is uniform with a tolerance within about 25%, or within about 20%, or within about 15%, or within about 10%, or within about 5%, or within about 3%, or within about 1%, or less than 1%, throughout the entire length of the continuous loop. In some embodiments, the one or more suture lines used to form the one or more continuous loops each also advantageously have substantially uniform flexibility along the length of the suture line. For example, a suture line forming a continuous loop can be formed so as to be free from any rigid sections differing in flexibility from a more flexible section by more than about 20%, about 15%, about 10%, about 5%, or about 1% (e.g., as measured using a standard stiffness test).

The embodiments illustrated in FIGS. 2A-2E, as well as other embodiments disclosed herein, show bone anchors configured to be placed within bone so that the eyelet is disposed below the bone surface. For example, a threaded, cannulated bone anchor can be disposed within a portion of bone so that the eyelet of the anchor sits below the bone surface, thereby bringing target tissue into contact or near contact with the bone surface when fixated using attached suture line material. Alternative embodiments include one or more bone anchors positioned with an eyelet extending beyond a bone surface in a superficial position. Other bone anchors known in the art of orthopedic surgery may be used as desired, such as fully threaded anchors with suture attachment means positioned within an interior bore of the anchor. Accordingly, embodiments described and/or illustrated herein may utilize bone anchors of various types, and alternative bone anchors may be substituted for and/or combined with the illustrated bone anchors.

Figure 3A:
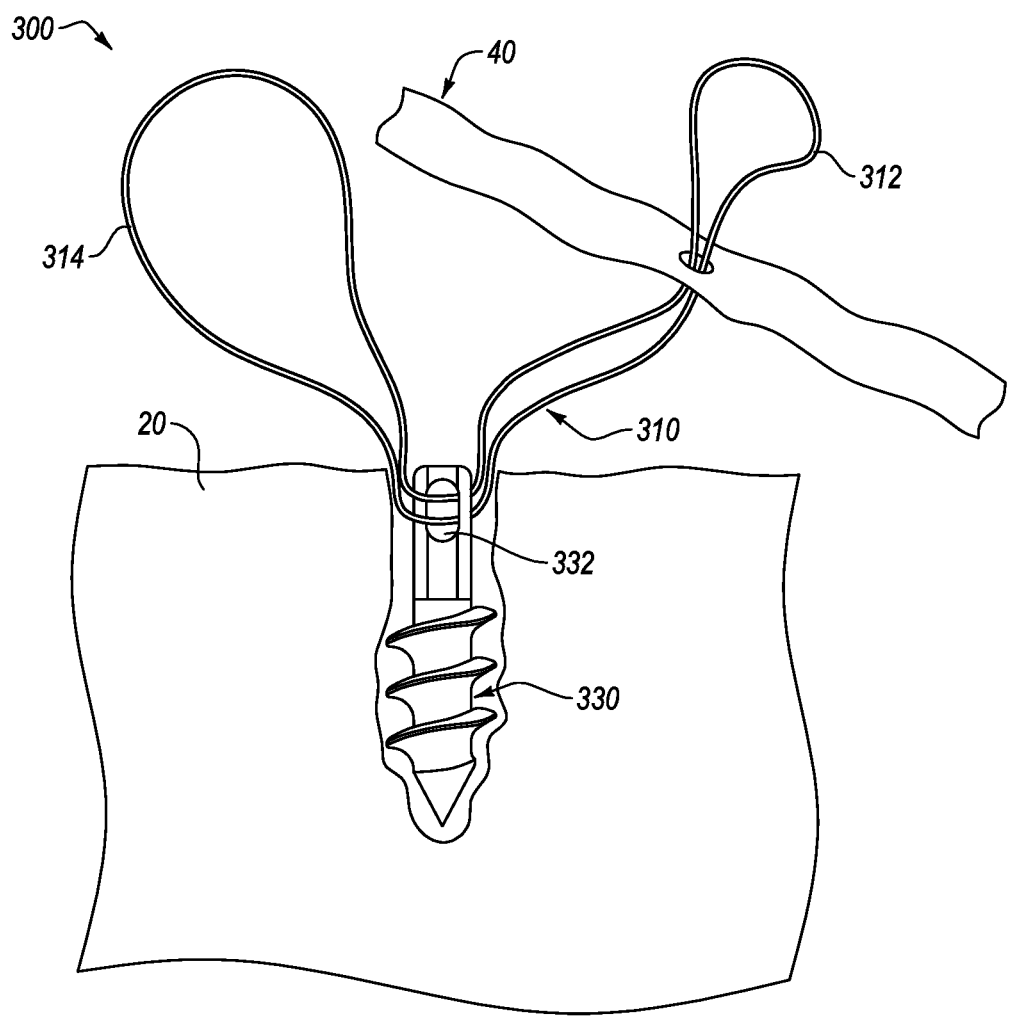
FIGS. 3A-3C illustrate another assembly and method according to the present disclosure for joining target tissue to bone.
Figure 3B:
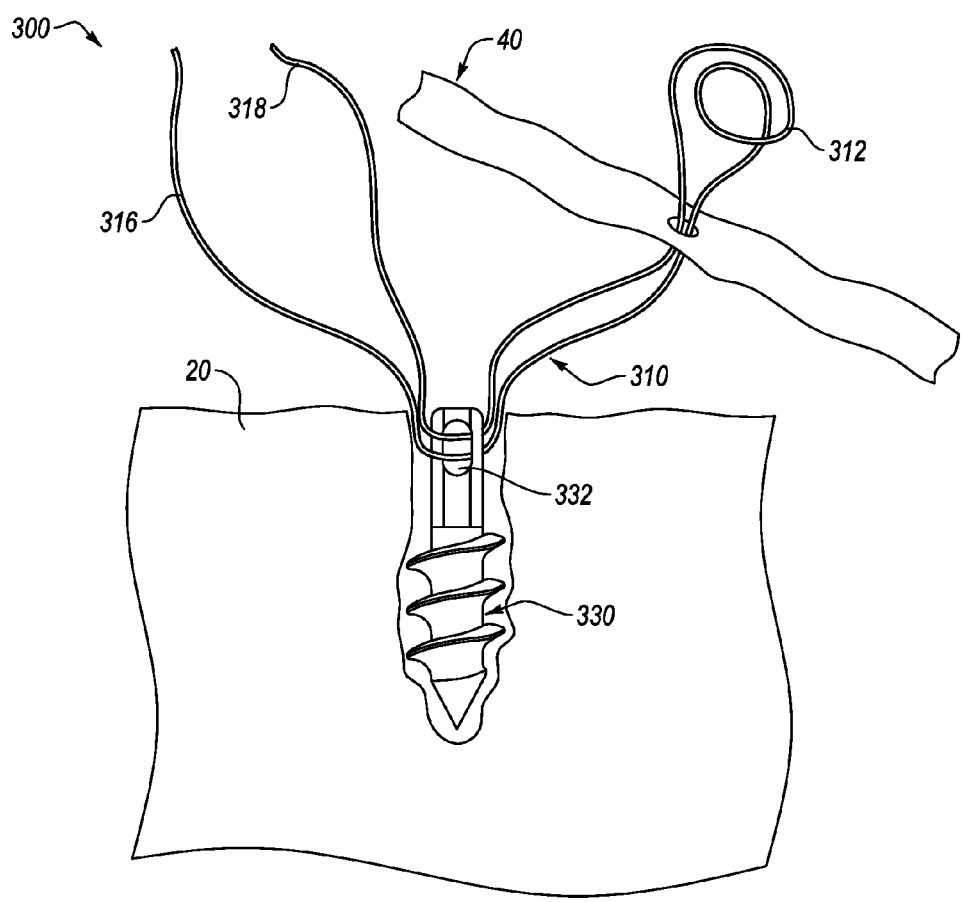
Figure 3C:
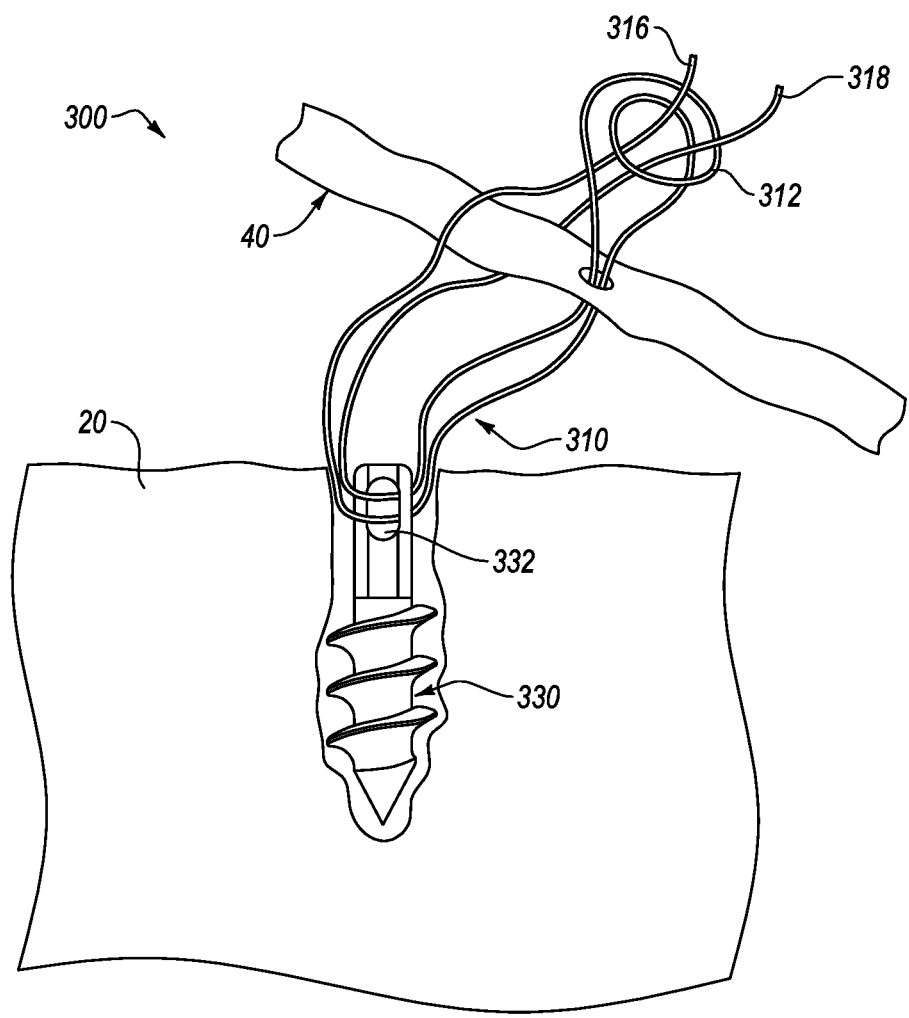

FIGS. 3A-3C illustrate another embodiment of an orthopedic ligation assembly 300 of the present disclosure. The embodiment illustrated in FIGS. 3A-3C is particularly useful in a percutaneous biceps tenodesis procedure, though it may be used in other procedures (e.g., percutaneous or non-percutaneous) requiring the attachment of a tendon or ligament to bone as well.

FIG. 3A illustrates a suture line formed in a continuous loop 310 that is passed through an anchor 330 to form a first looped portion 312 extending from an eyelet 332 in the anchor 330 and a second looped portion 314 extending from the same eyelet 332 of the anchor 330 on an opposite side from the first looped portion 312. As shown in FIG. 3B, the first looped portion 312 may be passed through the target tissue 40 and one of the looped portions (e.g., the second looped portion 314) may be cut to form two tails 316 and 318. As illustrated in FIG. 3C, the tails 316 and 318 may be positioned around opposite sides of the target tissue 40. For example, a first tail 316 may be positioned around an upper side of the target tissue 40 while a second tail 318 is positioned around a lower side of the target tissue 40, (from the perspective of FIG. 3C). The target tissue 40 may then be secured to the bone 20 by passing the tails 316 and 318 through the looped portion 312 to form a knot to secure the target tissue 40 in place against the bone 20 and/or anchor 330.

Figure 4A:
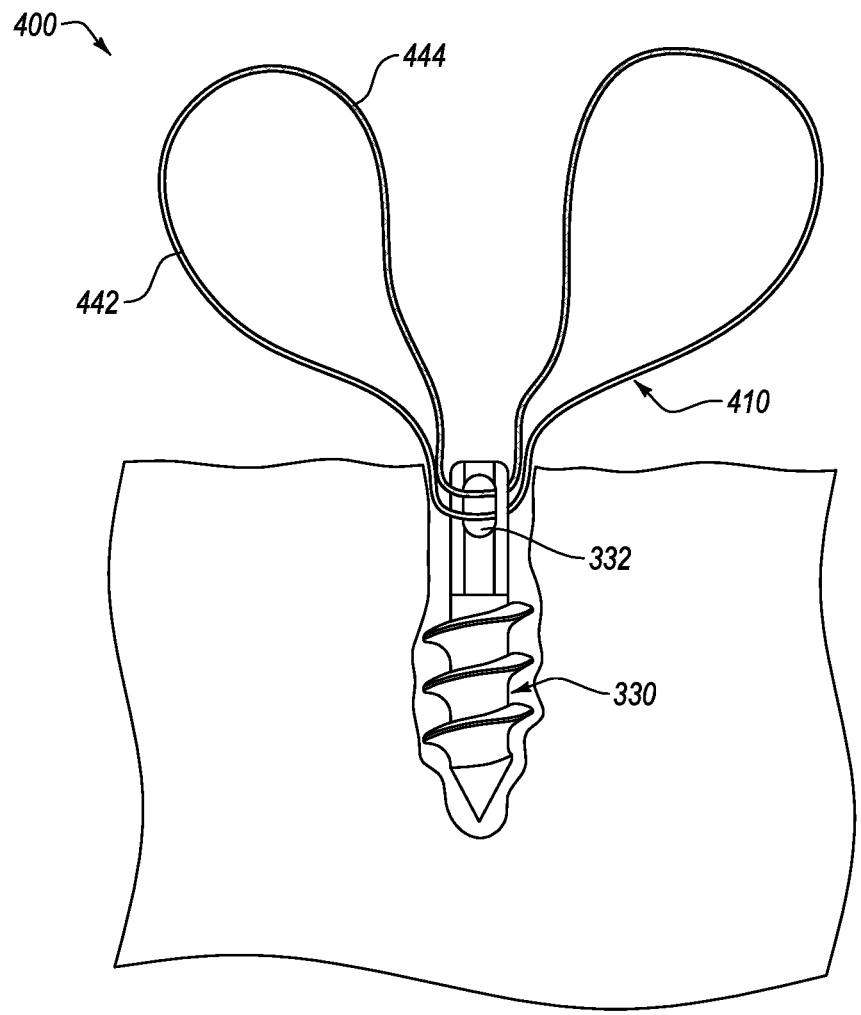
FIGS. 4A-4C illustrate another assembly and method according to the present disclosure having differentiable sections to aid in joining target tissue to bone.
Figure 4B:
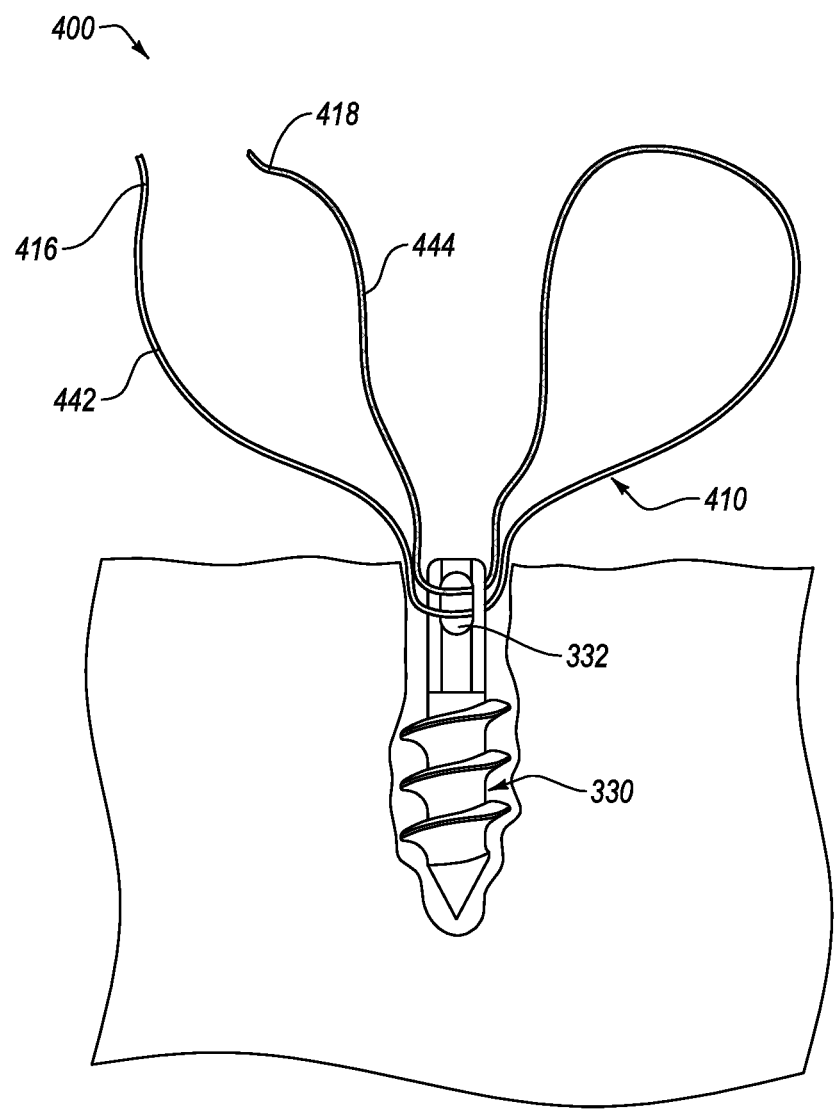
Figure 4C:
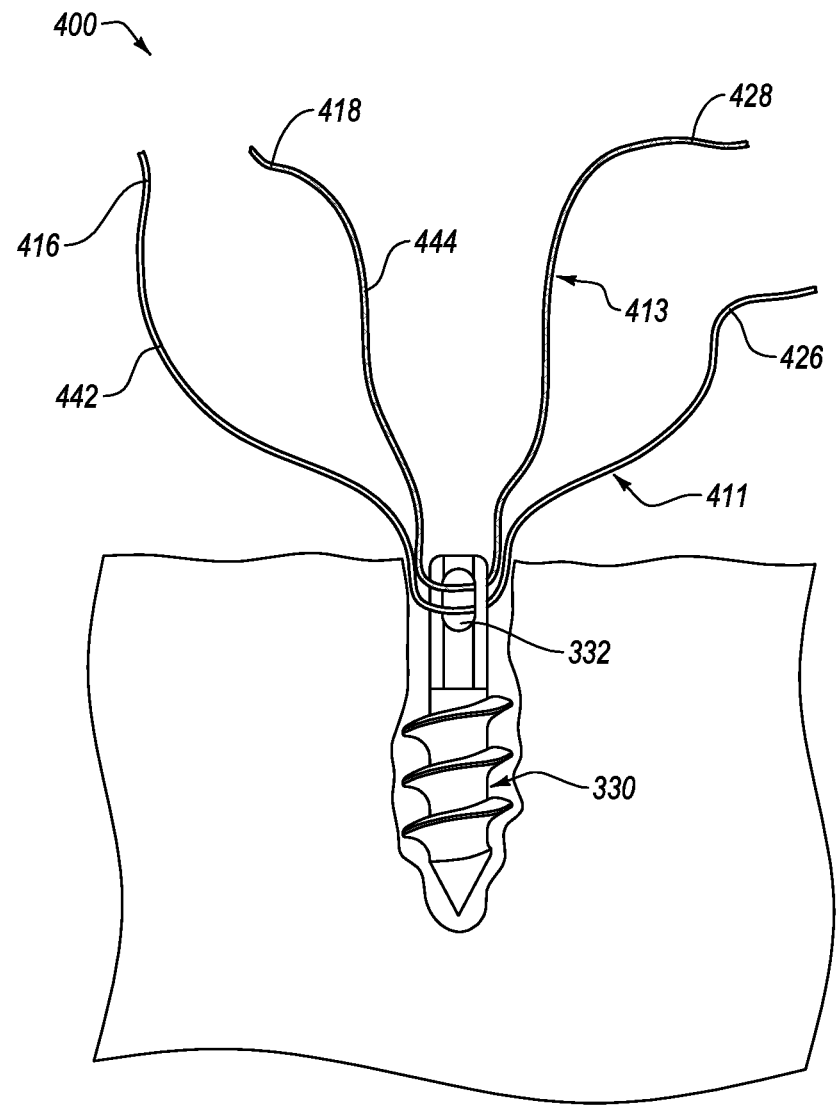

FIGS. 4A-4C illustrate another embodiment of an orthopedic ligation assembly 400. The illustrated embodiment can include a plurality of visually and/or tactily differentiable sections enabling a user to organize and/or position the suture line based on the differentiable sections. For example, as illustrated in FIG. 4A, a suture line can be formed as a continuous loop 410 having two differently patterned sections 442 and 444. In other embodiments, a suture line can include a plurality of sections that are differentiable based on color, pattern (e.g., striped, checkered, diamond, honeycomb, patched, streaked, smudged), and/or texture, for example.

As illustrated in FIG. 4B, the suture line having differentiable sections can be moved and/or oriented to a desired position and a looped portion can be cut to form two tails. For example, a looped portion of the suture line can be cut to form two tails at a junction between the separate differentiable sections 442 and 444, leaving a first tail 416 with a first differentiable feature and a second tail 418 with a second differentiable feature. The configuration illustrated in FIG. 4B allows a user to secure a target tissue to an anchor and/or bone surface by passing the remaining looped portion through the target tissue and passing the tails through the looped portion (e.g., as described by the foregoing and elsewhere herein).

In some embodiments, the remaining looped portion can also be cut. For example, as illustrated in FIG. 4C, the remaining looped portion can be cut at a second junction between the separate differentiable sections 442 and 444 to form a third tail 426 and a fourth tail 428. The resulting configuration includes a double-loaded anchor 430 having a first suture line 411 and a second suture line 413 passed through the same eyelet 432. In the illustrated embodiment, the first suture line 411 has the first differentiable feature 442, and the second suture line 413 has a second differentiable feature 444. In other embodiments, the resulting first and second suture lines may omit differentiable features or may include additional differentiable features. The resulting double loaded anchor configuration can allow a surgeon to perform a variety of standard ligation procedures known in the art based on such a non-looped suture line configuration.

Figure 5A:
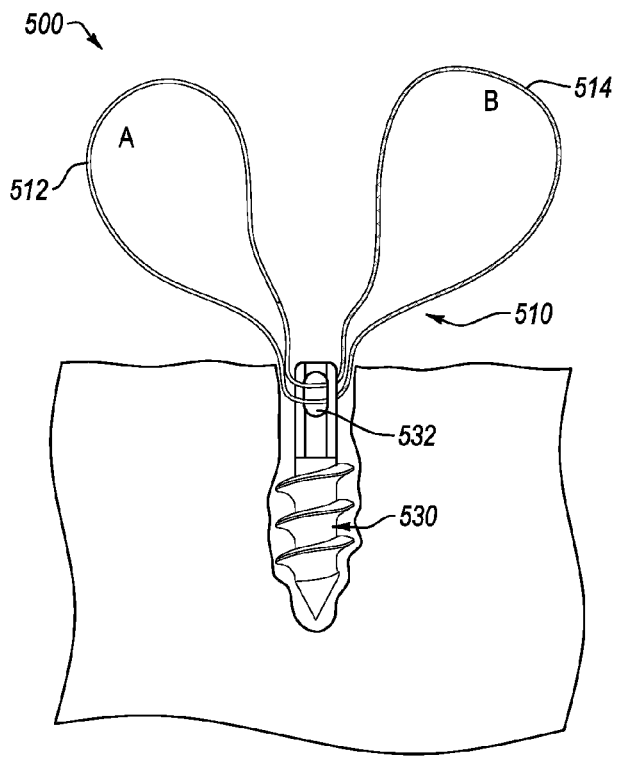
FIGS. 5A-5D illustrate exemplary configurations and orientations of continuous loop suture lines having differentiable features.
Figure 5B:
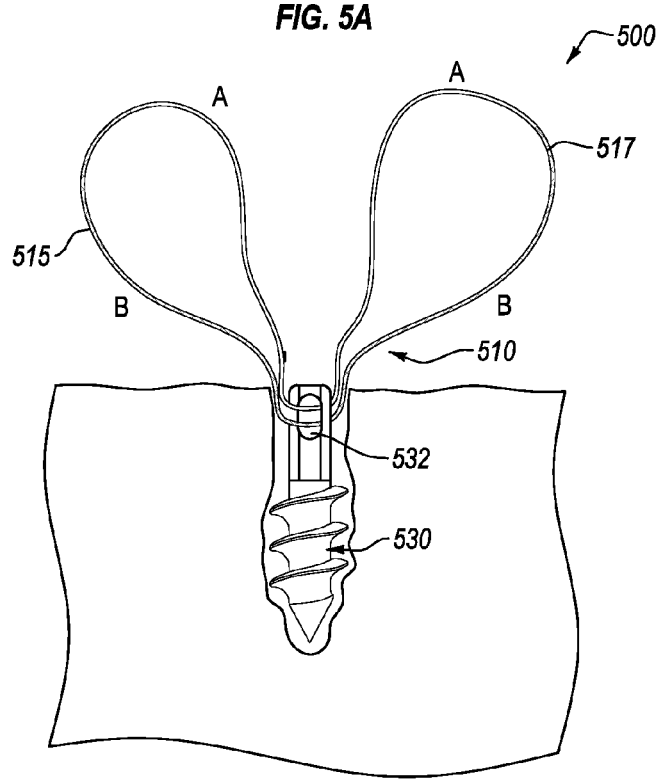

FIGS. 5A-5D illustrate exemplary configurations and suture line orientations of embodiments including two or more differentiable sections. FIG. 5A illustrates an embodiment of an assembly 500 with a suture line 510 having a first differentiable feature (A) on a first looped portion 512 on a first side of an eyelet 532 of an anchor 530, and a second differentiable feature (B) on a second looped portion 514 on a second side of the eyelet 532. FIG. 5B illustrates an embodiment similarly having differentiable features A and B, but with the differentiable features oriented differently relative to the eyelet 532 as compared to the embodiment of FIG. 5A. In the embodiment of FIG. 5B, each looped portion 515 and 517 includes a section having differentiable feature A and a section having differentiable feature B. In some embodiments, an anchor may be pre-loaded with a suture line in the configuration shown in FIG. 5A or FIG. 5B. In some embodiments, the suture line 510 shown in FIG. 5A can be repositioned to form the configuration shown in FIG. 5B, and vice versa, by repositioning the suture line 510 so that different sections pass through the eyelet 532 and different sections form the two looped portions.

Figure 5C:
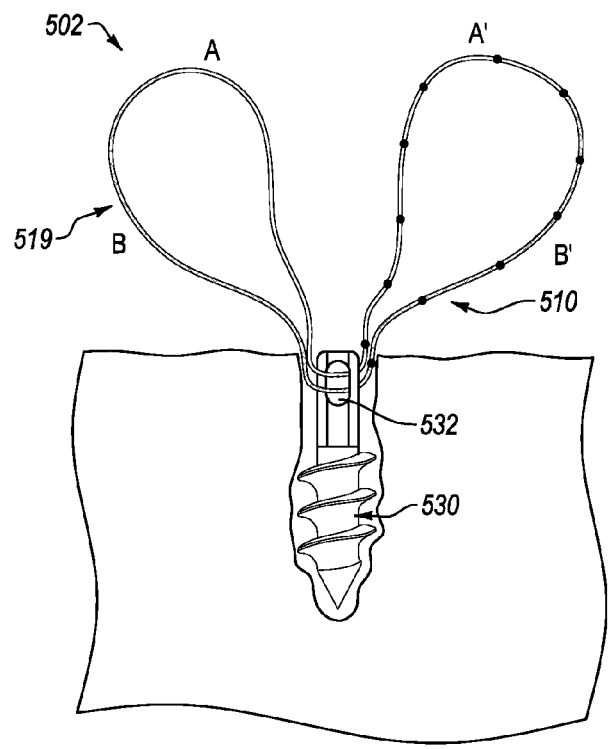
Figure 5D:
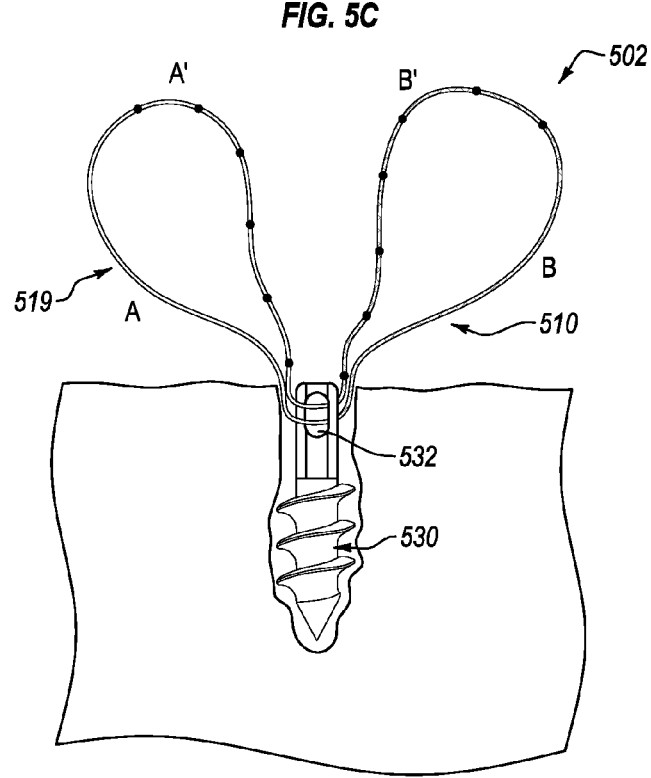

FIG. 5C illustrates an embodiment of an assembly 502 with a suture line 519 having first and second differentiable features (distinguishing A and A' from B and B') with a first sub-feature to distinguish A from A' and a second sub-feature to distinguish B from B'. For example, the first and second differentiable features may be distinguishable by color (e.g., A is a different color than B) and the sub-features may include stripes or other patterns overlaying the color (to form A' and B'). FIG. 5D illustrates another embodiment of a suture line 519 having differentiable features and sub-features to form sections A, A', B, and B'. In some embodiments, an anchor 530 may be pre-loaded with a suture line 519 in the configuration shown in FIG. 5C or 5D. In some embodiments, the suture line 519 as shown in FIG. 5C can be repositioned to form the configuration shown in FIG. 5D, and vice versa, by repositioning the suture line 519 so that different sections pass through the eyelet 532 and different sections form the two looped portions.

The embodiments of FIGS. 5A-5D show a bone anchor configuration where the bone anchor is configured to be placed at or below the bone surface (e.g., so that the eyelet or proximal end resides at or below the bone surface). Other embodiments may include anchors configured to be superficially positioned.

Embodiments described herein provide a number of advantages and benefits. For example, an orthopedic ligation assembly having a suture line with a continuous loop structure loaded through an anchor can provide a user with a variety of options for securing the target tissue to the anchor and/or bone surface. For example, the same orthopedic ligation assembly can be used to perform a procedure requiring a looped portion and two tails, or to perform a procedure requiring a double loaded anchor configuration having two separate suture lines.

The embodiment illustrated in FIGS. 2-5 show a single continuous loop suture line loaded onto the bone anchor. In other embodiments, one or more additional suture lines may also be loaded onto the bone anchor or may be pre-loaded onto the bone anchor and provided with the bone anchor. For example, a bone anchor may be loaded or pre-loaded with a first suture line in the form of a continuous loop, and a second suture line in the form of a standard single thread. In such embodiments, the first suture line, provided in the form of a continuous loop, can be used as described above, while the second suture line, provided in the form of a standard thread, can be used to form a variety of additional ligature procedures known in the art. In other embodiments, further suture line strands and/or additional continuous loop suture lines can also be included (e.g., three, four, five, or more suture lines in the form of single strands and/or continuous loops).

In addition, an orthopedic ligation assembly of the present disclosure can be used in a suture tape ligation procedure. For example, the suture line or suture tape material can be passed from a first anchor over the target tissue and to a second anchor or back to the first anchor in order to secure the target tissue to the bone, rather than passing through the target tissue. This versatility in the number of useful functions can reduce the number of different tissue ligation components a health care provider or health care facility must keep on hand, allowing for a more consolidated inventory and more simplified supply chain management, as well as providing associated cost savings.

Some embodiments include multiple continuous loop suture lines loaded onto a single anchor. For example, some embodiments include two or more continuous loops loaded onto an anchor, each continuous loop passing through an eyelet of the anchor to form a first looped portion extending from one side of the eyelet and a second looped portion extending from an opposite side of the same eyelet. In some embodiments, an anchor may be double-loaded, triple-loaded, quadruple-loaded, or further loaded with continuous loop suture lines in this manner.

II. Anchor Unloading Prevention

Figure 6:
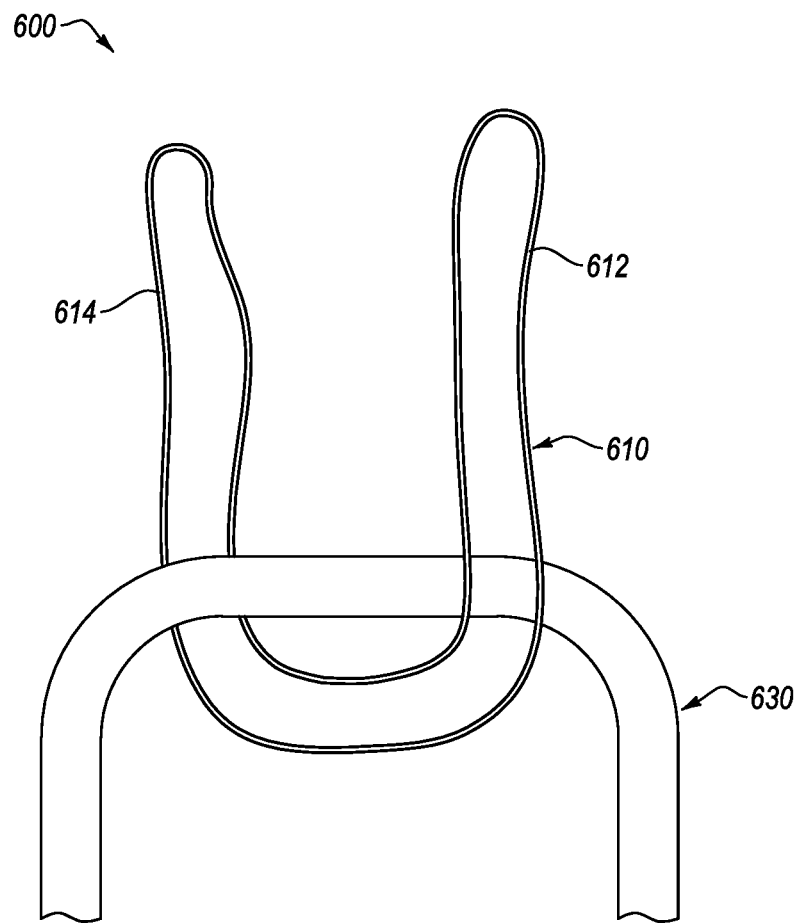
FIG. 6 illustrates a suture line and anchor configuration wherein the suture line is capable of being unloaded from the anchor by pulling on one portion of the suture line.

Tissue ligation assemblies of the present disclosure can also include anchors which can be loaded, or which can be pre-loaded (e.g., connected with the anchor prior to implantation of the anchor), with a suture line in a configuration that prevents unloading of the suture line from the anchor. FIG. 6 illustrates an embodiment of an assembly 600 having a configuration capable of being unloaded. For example, in the illustrated configuration, the looped suture line 610 can be unloaded from the anchor 630 by pulling the first or second looped portion 612 or 614 and allowing the opposite looped portion to pass completely through the anchor 630.

Figure 7A:
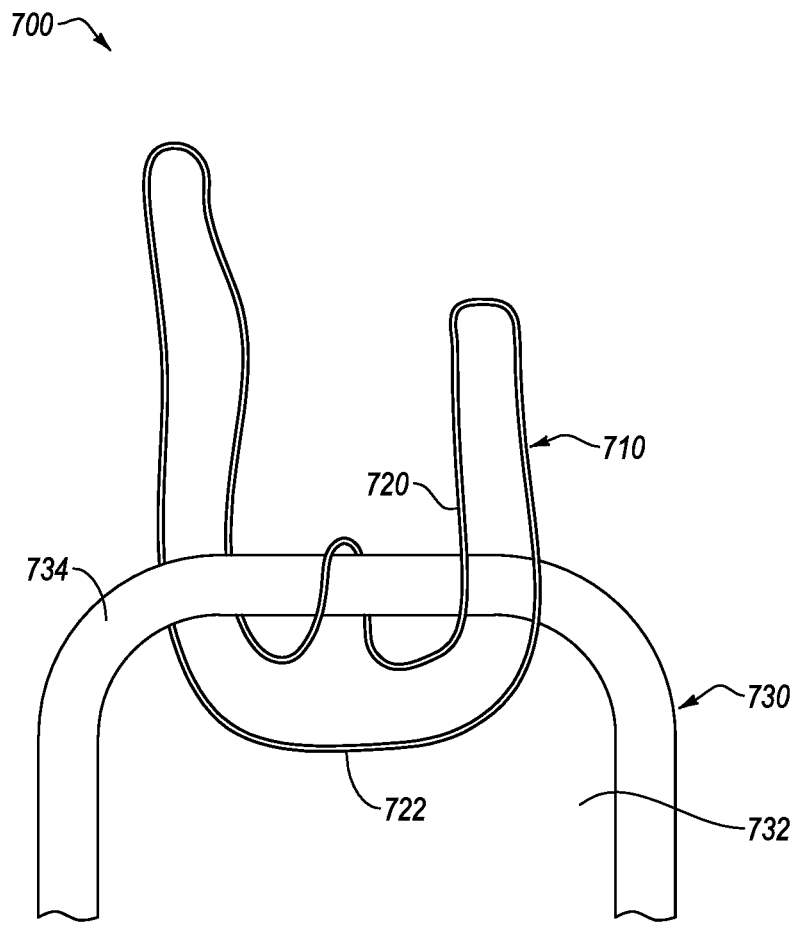
FIGS. 7A-7D illustrate a suture line and anchor configuration wherein the suture line is prevented from being unloaded from the anchor by pulling on one portion of the suture line.
Figure 7B:
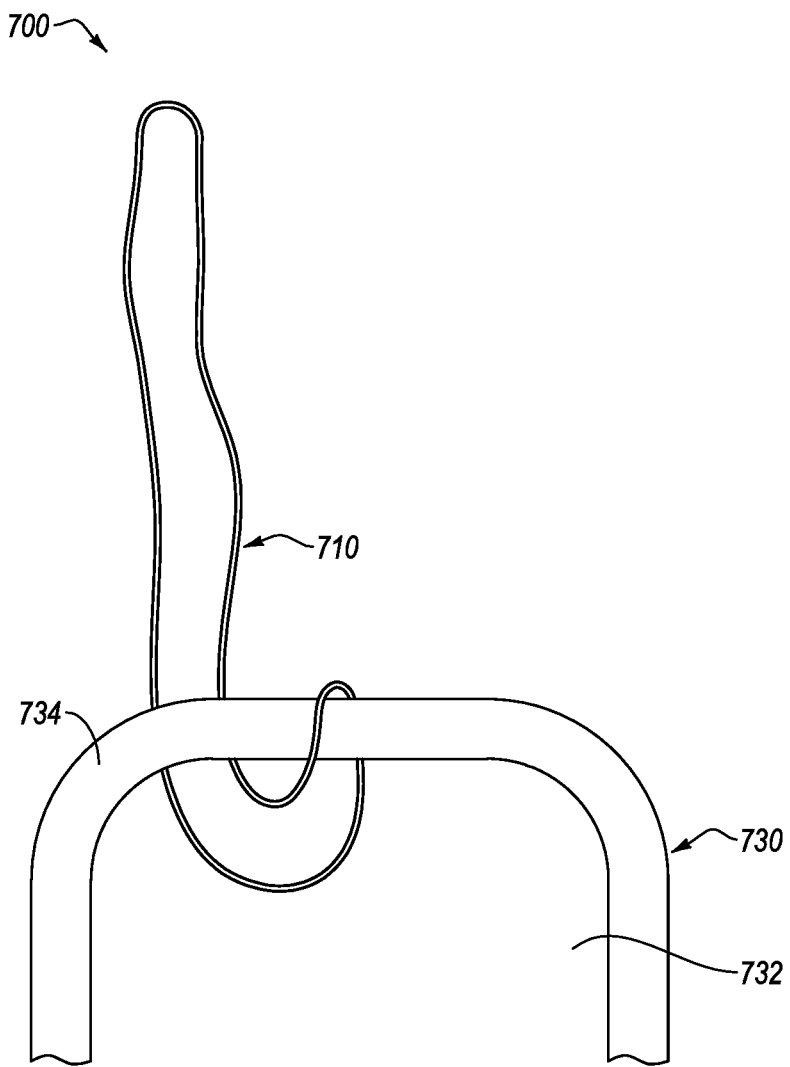
Figure 7C:
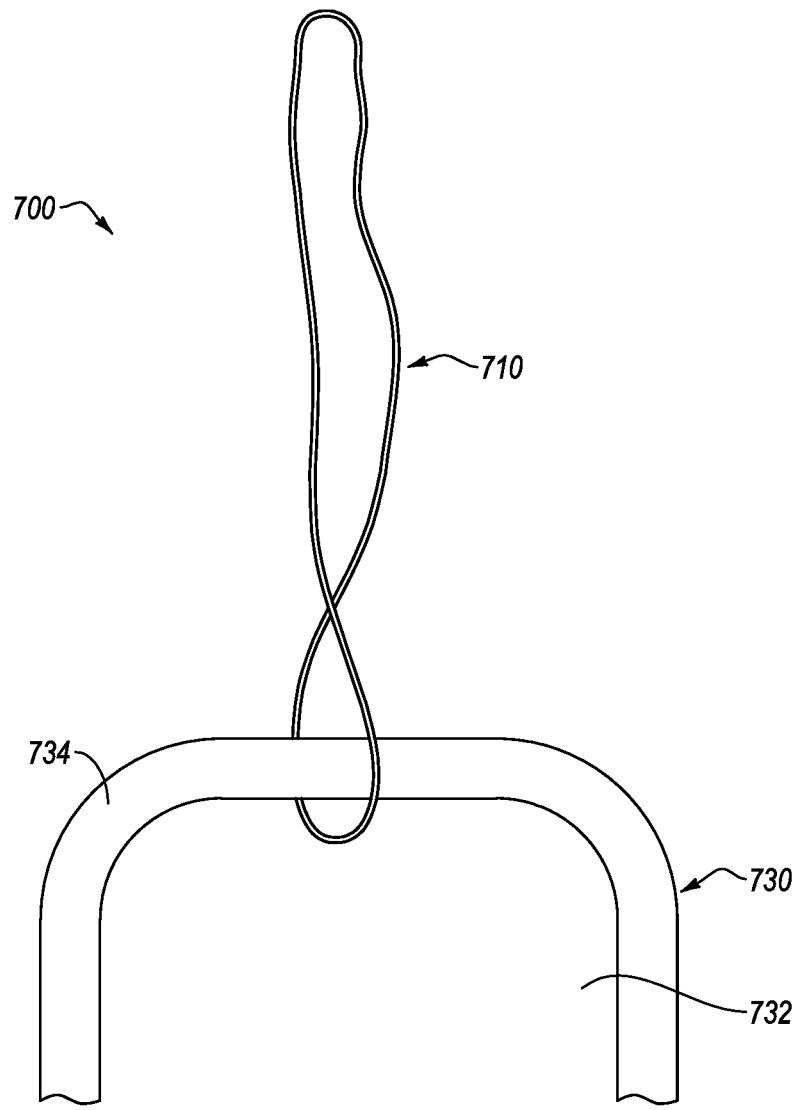
Figure 7D:
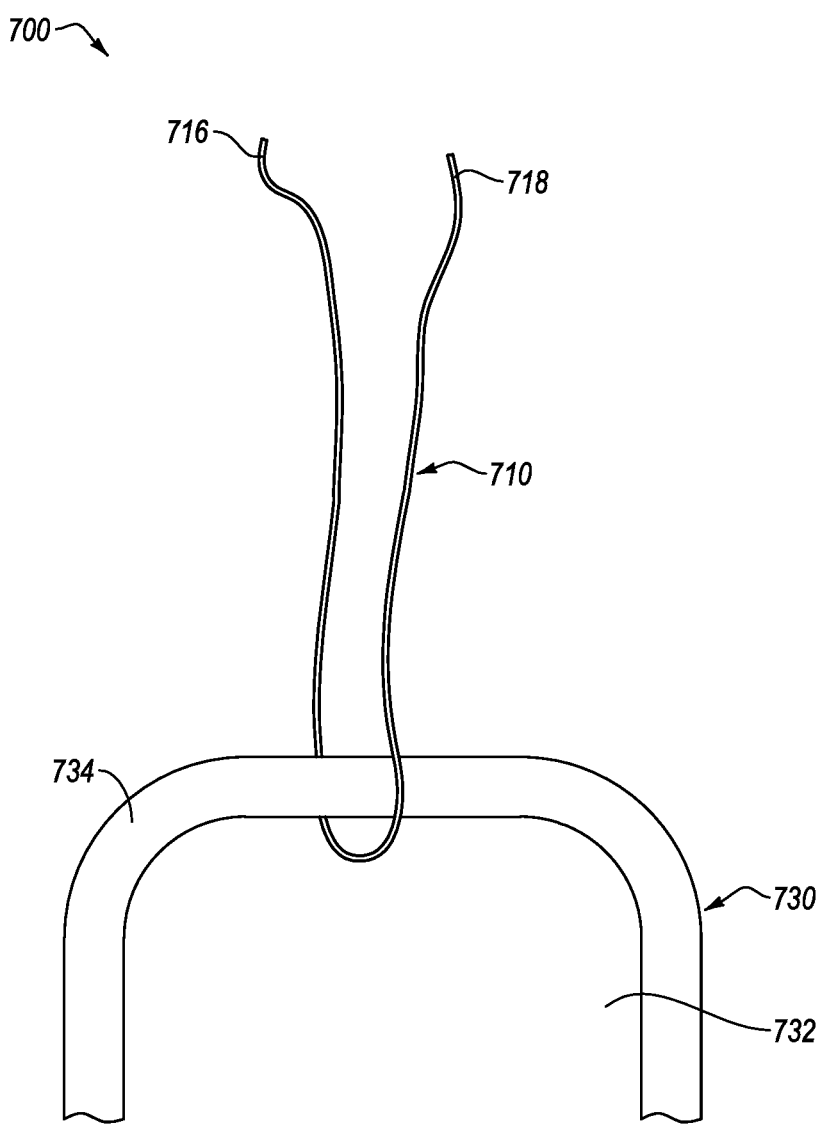

FIGS. 7A-7D illustrate an alternative embodiment of an assembly 700 having a configuration that prevents unloading of the suture line 710 from the anchor. As illustrated in FIG. 7A, an anchor 730 can be loaded such that a first strand 720 of a looped suture line 710 is passed into the eyelet 732, wrapped around a rim 734 of the eyelet 732, and passed out of the eyelet 732, while a second strand 722 of the looped suture line 710 is passed through the eyelet 732 without being wrapped around the rim 734 of the eyelet. In this configuration, the looped suture line 710 cannot become accidentally unloaded and detached from the anchor 730 through pulling a portion of the looped suture line 710 too far from the anchor 730. For example, upon pulling one end of the suture line 710, the configurations shown in FIG. 7B and then FIG. 7C will result. As illustrated, rather than the suture line 710 becoming completely detached from the anchor 730 and rendering the anchor 730 and suture assembly 700 useless, these configurations still allow a surgeon to make use of the anchor 730 and suture line 710. For example, as illustrated in FIG. 7D, a surgeon could cut the suture line 710 to provide a standard single-loaded anchor configuration with two tails 716 and 718.

Figure 8A:
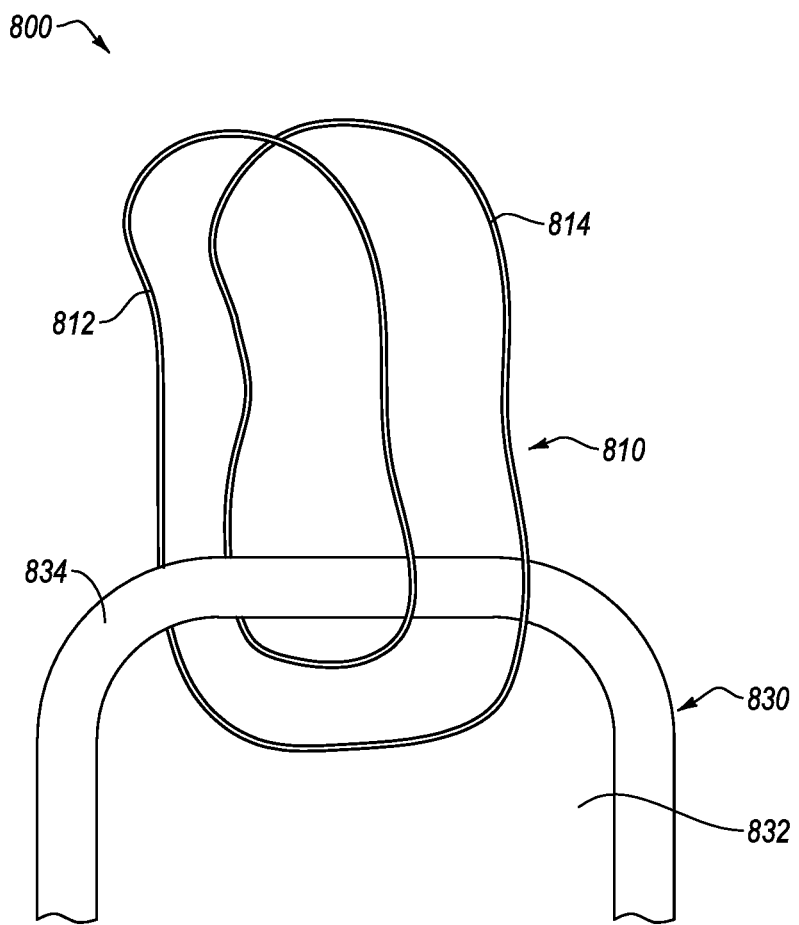
FIGS. 8A-8C illustrate another suture line and anchor configuration wherein the suture line is prevented from being unloaded from the anchor by pulling on one portion of the suture line.
Figure 8B:
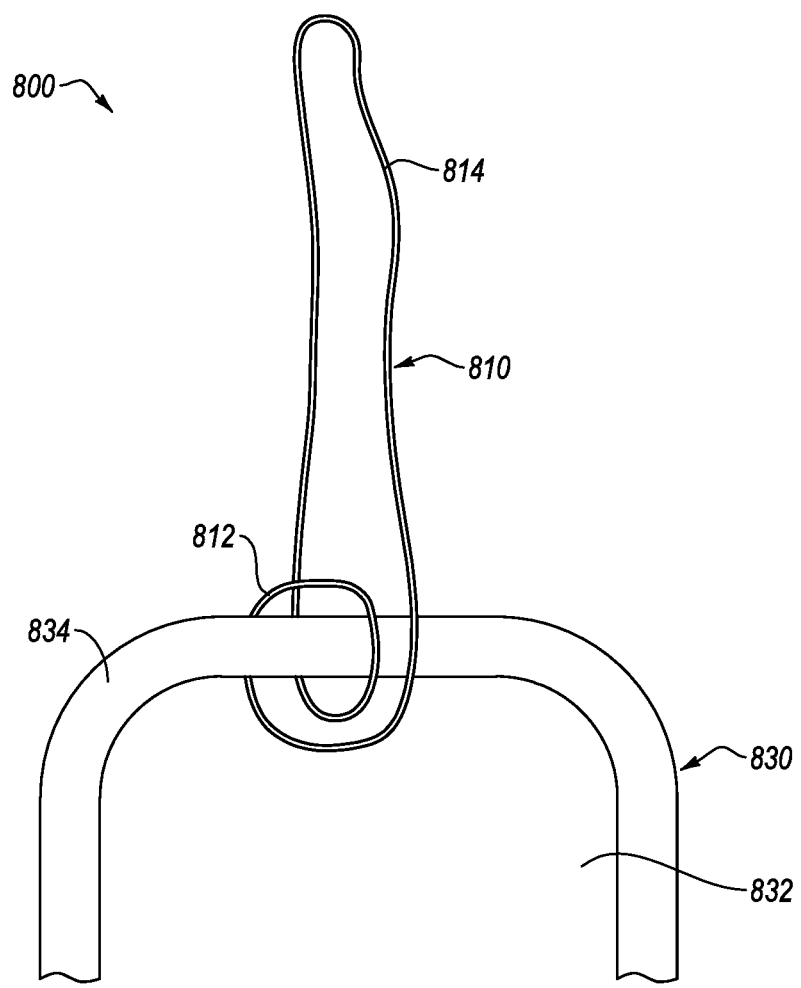
Figure 8C:
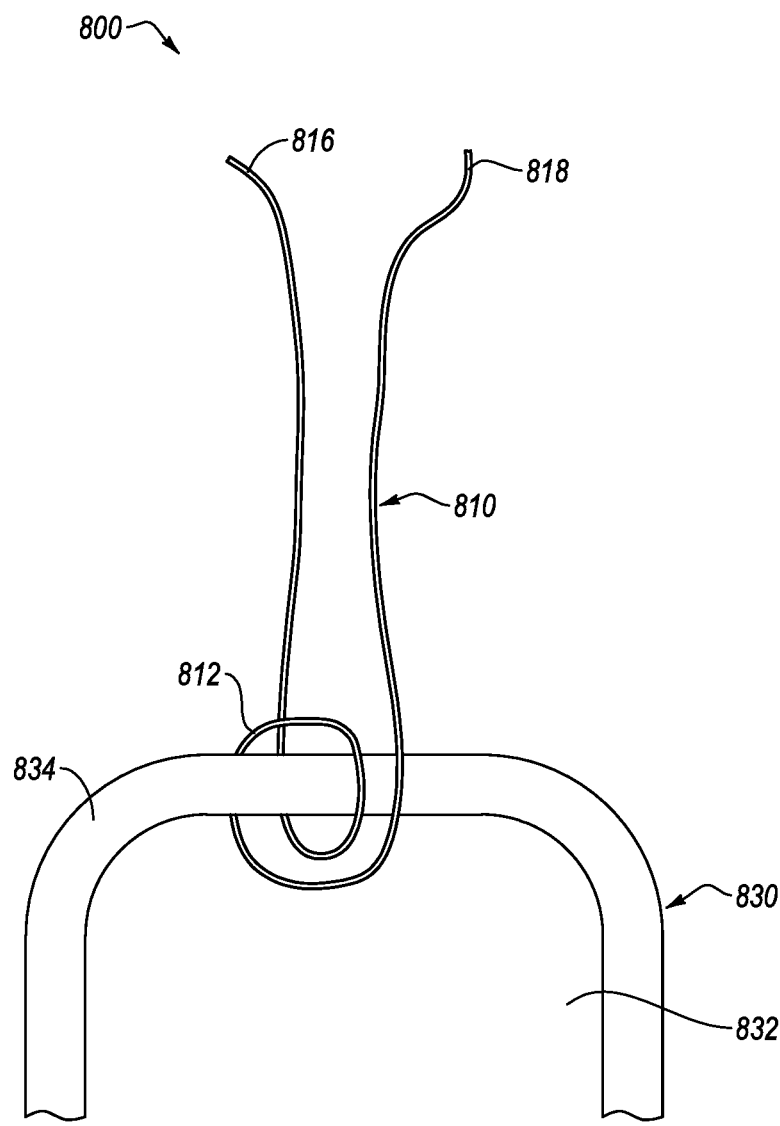
Figure 4A:
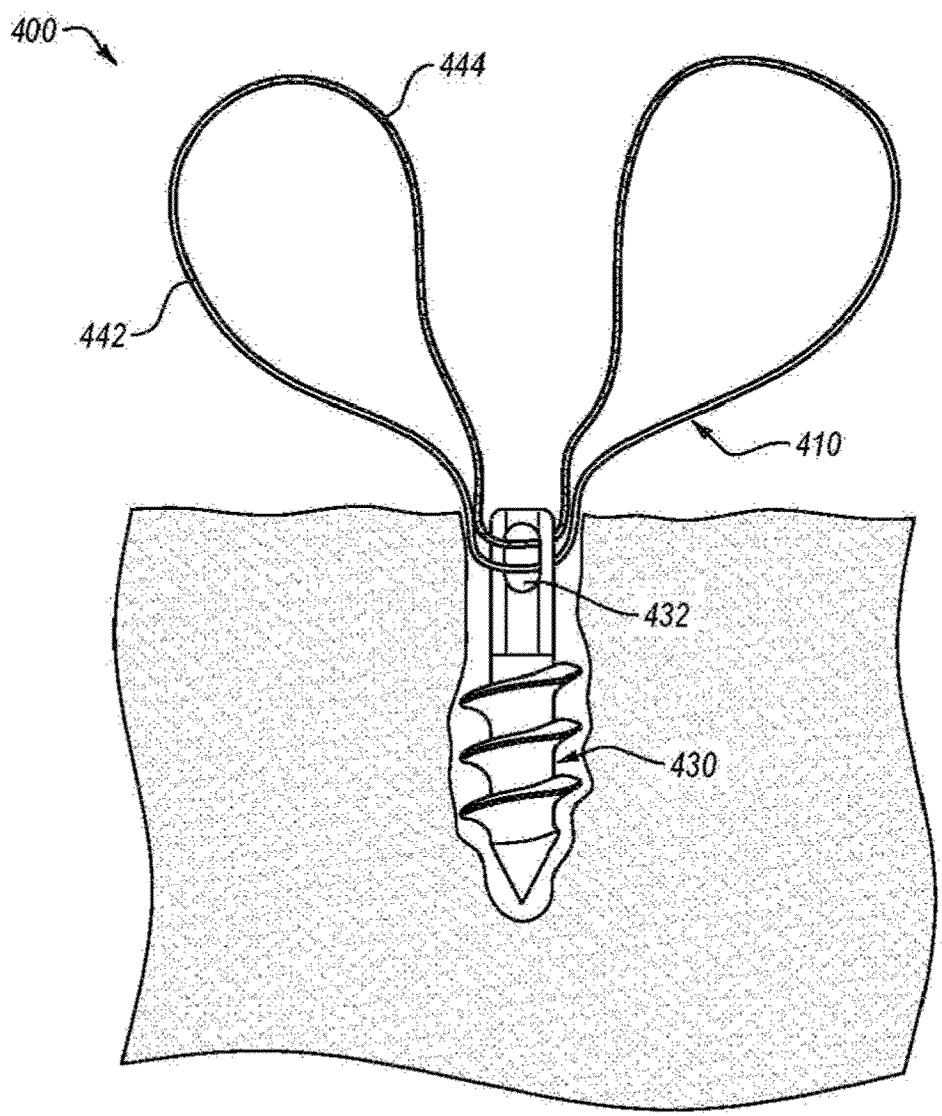
Figure 4B:
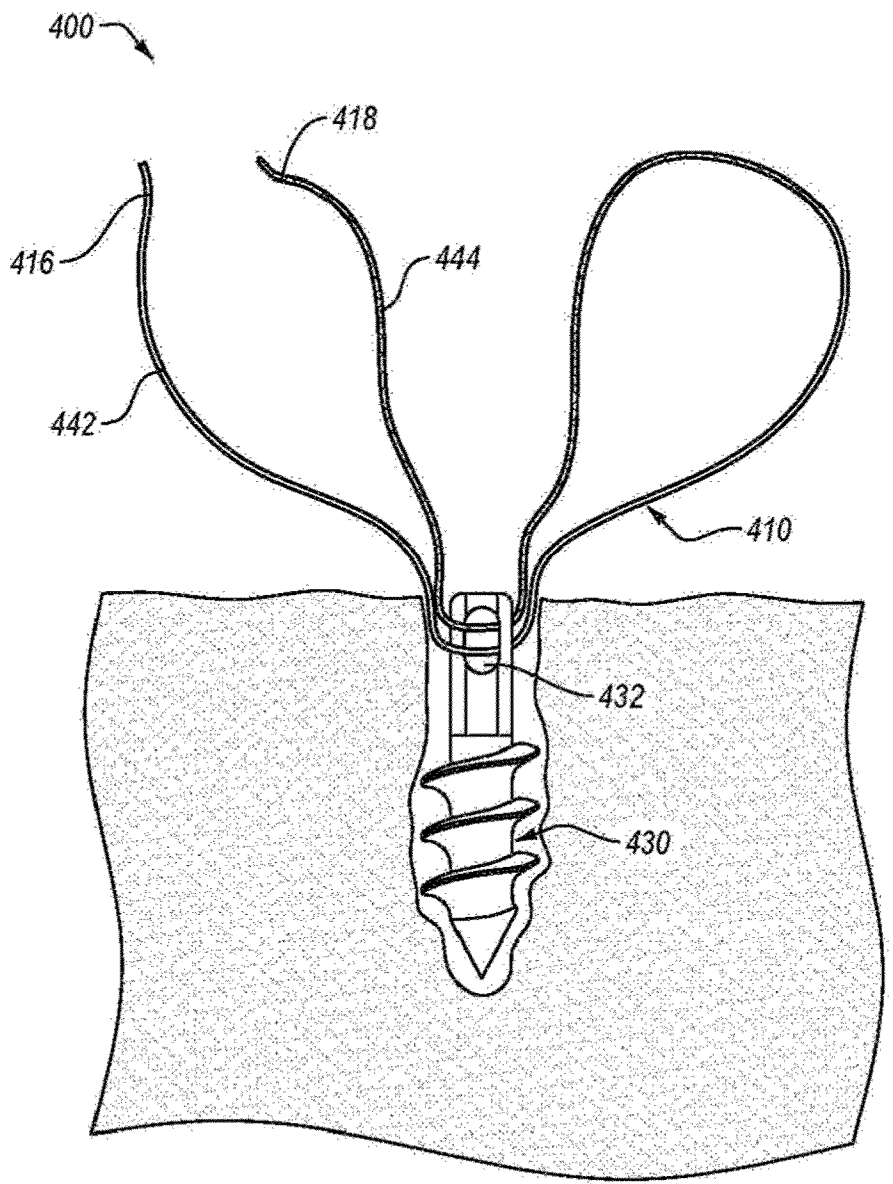
Figure 4C:
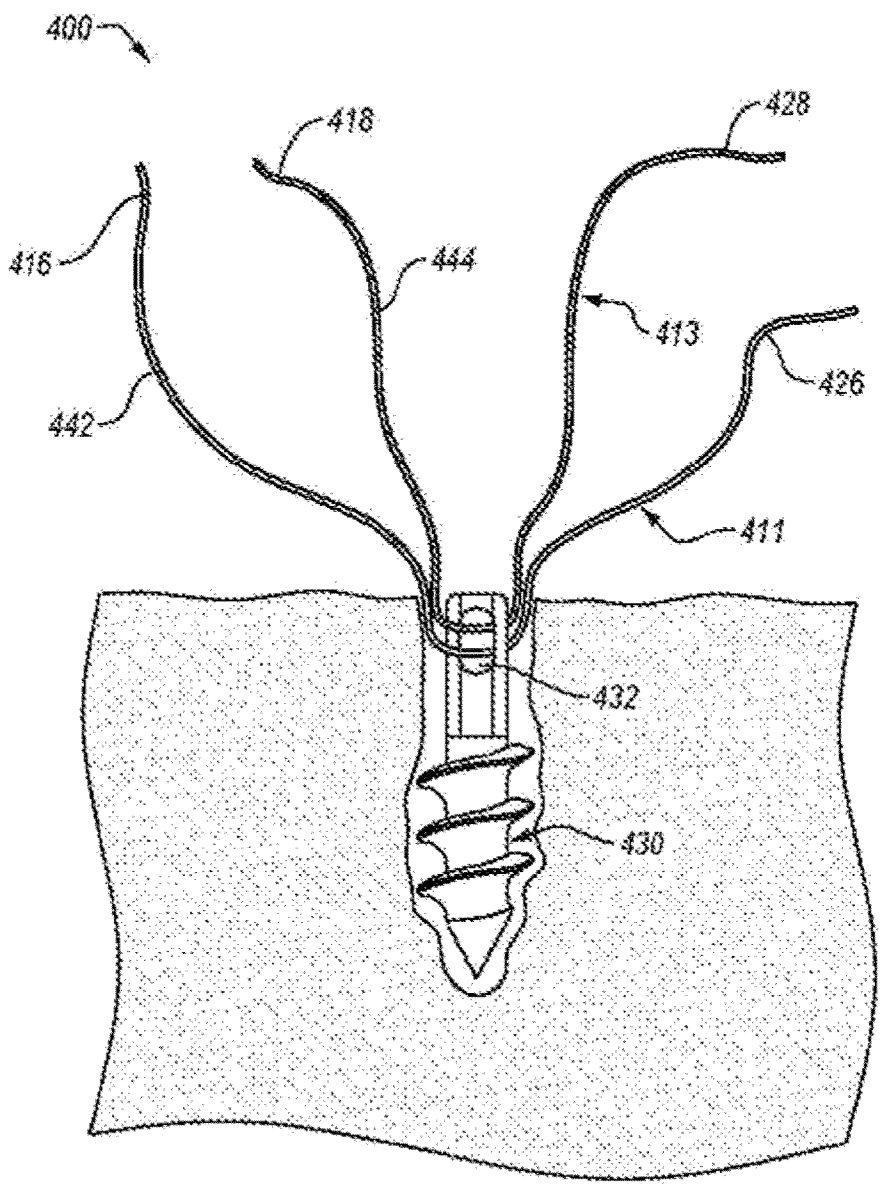

FIGS. 8A-8C illustrate another embodiment of an assembly 800 having a configuration that prevents unloading of the suture line 810 from the anchor 830. As illustrated in FIG. 8A, an anchor 830 can be loaded such that a suture line 810 is passed through the eyelet 832 of the anchor 830 from a first side of the eyelet 832 to a second side of the eyelet 832, and is looped around and passed through the eyelet 832 a second time from the first side of the eyelet 832 to the second side of the eyelet 832, before being looped around to close the continuous loop structure of the suture line 810. In other words, the continuous loop suture line 810 can be oriented in a figure 8 configuration, and a rim 834 of the eyelet 832 can pass through each of the separate circlets 812 and 814 of the figure 8 configuration (e.g., by folding the figure 8 down to form two adjacent hoops or circlets) to form the configuration shown in FIG. 8A.

In the configuration shown in FIG. 8A, the suture line 810 cannot become accidentally unloaded from the anchor 830 through pulling a portion of the looped suture line 810 too far from the anchor 830. For example, upon pulling one end of the suture line 810, the configurations shown in FIG. 8B will result. As illustrated, rather than the suture line 810 becoming completely detached from the anchor 830 and rendering the anchor 830 and suture assembly 800 useless, the configuration still allows a surgeon to make use of the anchor 830 and suture line 810. For example, a surgeon could readjust the suture line 810 by pulling the smaller looped portion 812 (i.e., the looped portion 812 that is wrapped more tightly around the rim 834 of the eyelet 832) to manipulate and reposition the suture line 810 toward the configuration illustrated in FIG. 8A. Alternatively, a surgeon could cut the longer looped portion 814 to provide the configuration illustrated in FIG. 8C, resulting in a configuration with two tails 816 and 818 and a double-wrapped loading onto the anchor.

In some embodiments, tissue ligation assemblies having configurations that prevent unloading of the suture line from the anchor are pre-loaded. For example, a suture line may be positioned through an eyelet of on an anchor (e.g., as in the embodiments of FIG. 7A or 8A) prior to the eyelet being fused or otherwise sealed into a closed shape, and/or prior to the suture line being fused or otherwise sealed into its closed, continuous loop shape. Such pre-loaded assemblies can then be provided prior to the implantation of the anchor during a tissue ligation procedure or other compatible orthopedic procedure.

The terms "approximately," "about," and "substantially," as used herein, represent an amount or condition close to the stated amount or condition that still performs a desired function or achieves a desired result. For example, the terms "approximately," "about," and "substantially" may refer to an amount that is within less than 10% of, within less than 1% of, within less than 0.1% of, and within less than 0.01% of a stated amount. In addition, unless expressly described otherwise, all amounts (e.g., angle measurements, dimensions measurements, etc.) are to be interpreted as being "approximately," "about," and/or "substantially" the stated amount, regardless of whether the terms "approximately," "about," and/or "substantially."

Additionally, elements described in relation to any embodiment depicted and/or described herein may be combinable with elements described in relation to any other embodiment depicted and/or described herein. For example, any element described in relation to an embodiment depicted in FIGS. 7A-8C may be combinable with an embodiment described in relation to FIGS. 2A-5D.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An orthopedic ligation assembly, comprising:
   a bone anchor having an eyelet; and
   a suture line formed in a continuous loop and loaded onto the bone anchor, the suture line passing through the eyelet of the bone anchor and arranged to form a first looped portion extending from a first side of the eyelet of the bone anchor and a second looped portion extending from a second side of the eyelet of the bone anchor,
   wherein a first portion of the suture line passes through the first side of the eyelet, wraps around a rim of the eyelet, and passes out the second side of the eyelet, and
   wherein a second portion of the suture line passes through the first side of the eyelet and passes out the second side of the eyelet without being wrapped around the rim.

2. The assembly of claim 1, wherein the suture line has a cross-section that does not differ in diameter along an entire length of the suture line by more than 15%.

3. The assembly of claim 1, wherein the suture line has a cross-section that does not differ in diameter along an entire length of the suture line by more than 5%.

4. The assembly of claim 1, wherein the suture line is free of rigid sections.

5. The assembly of claim 1, wherein the suture line is free of rigid sections differing in flexibility from a more flexible section by more than 15%.

6. The assembly of claim 1, wherein the suture line is passed through the eyelet such that two strand portions of the suture line reside within the eyelet.

7. The assembly of claim 1, wherein the suture line is loaded onto the bone anchor in a configuration that prevents unloading of the suture line from the anchor.

8. The assembly of claim 1, wherein the first portion of the suture line wraps once around the rim of the eyelet before passing out the second side of the eyelet.

9. The assembly of claim 1, wherein the bone anchor is pre-loaded with the suture line prior to implantation of the bone anchor.

10. The assembly of claim 1, wherein the eyelet of the bone anchor forms a fully closed shape.

11. The assembly of claim 1, wherein the suture line includes a plurality of differentiable sections.

12. The assembly of claim 11, wherein a first differentiable section has a first differentiable feature and a second differentiable section has a second differentiable feature, at least one of the first and second differentiable sections also including a differentiable sub-feature.

13. The assembly of claim 11, wherein the differentiable sub-feature is configured to distinguish one end of a differentiable section from an opposite end of the differentiable section.

14. An orthopedic ligation assembly, comprising:
a bone anchor having an eyelet; and
a suture line formed in a continuous loop and loaded onto the bone anchor, the suture line passing through the eyelet of the bone anchor and arranged to form a first looped portion extending from a first side of the eyelet of the bone anchor and a second looped portion extending from a second side of the eyelet of the bone anchor;
wherein the suture line includes a plurality of differentiable sections, wherein the suture line is arranged so that the first looped portion extending from the first side of the eyelet includes a first differentiable section and the second looped portion extending from the second side of the eyelet includes a second differentiable section different than the first differentiable section.

15. The assembly of claim 14, wherein the first differentiable section has a first visually differentiable feature and the second differentiable section has a second visually differentiable feature different than the first visually differentiable feature.

16. The assembly of claim 14, wherein at least one of the first and second differentiable sections also includes a differentiable sub-feature.

17. The assembly of claim 14, wherein a first portion of the suture line passes into the eyelet, wraps around a rim of the eyelet, and passes out the second side of the eyelet, and wherein a second strand of the suture line is passed through the eyelet without being wrapped around the rim of the eyelet.

18. An orthopedic ligation assembly, comprising:
a bone anchor having an eyelet; and
a suture line formed in a continuous loop and loaded onto the bone anchor the suture line passing through the eyelet of the bone anchor and arranged to form a first looped portion extending from a first side of the eyelet of the bone anchor and a second looped portion extending from a second side of the eyelet of the bone anchor,
wherein a first portion of the suture line passes through a first side of the eyelet, wraps around a rim of the eyelet, and passes out a second side of the eyelet,
wherein a second portion of the suture line passes through the first side of the eyelet and passes out the second side of the eyelet without being wrapped around the rim,
wherein the first looped portion has a first differentiable feature and the second looped portion has a second differentiable feature.

* * * * *

UNITED STATES PATENT AND TRADEMARK OFFICE
CERTIFICATE OF CORRECTION

PATENT NO. : 10,022,119 B2
APPLICATION NO. : 15/152834
DATED : July 17, 2018
INVENTOR(S) : Benjamin Widmer It is certified that error appears in the above-identified patent and that said Letters Patent is hereby corrected as shown below:

In the Drawings

Sheet 12, replace Fig. 4A with the figure as shown on the attached sheet, where reference number "332" has been replaced with reference number –432– and reference number "330" has been replaced with reference number –430–

Sheet 13, replace Fig. 4B with the figure as shown on the attached sheet, where reference number "332" has been replaced with reference number –432– and reference number "330" has been replaced with reference number –430–

Sheet 14, replace Fig. 4C with the figure as shown on the attached sheet, where reference number "332" has been replaced with reference number –432– and reference number "330" has been replaced with reference number –430–

In the Specification

Column 10
Line 33, after "substantially" insert --are used--

Signed and Sealed this
Twenty-sixth Day of February, 2019

Andrei Iancu
*Director of the United States Patent and Trademark Office*